(12) United States Patent
Boone, III et al.

(10) Patent No.: US 8,986,323 B2
(45) Date of Patent: Mar. 24, 2015

(54) MICRODERMABRASION SYSTEM UPGRADE KIT

(75) Inventors: N. Brendon Boone, III, Encino, CA (US); Basil M. Hantash, East Palo Alto, CA (US); Kenneth B. Karasiuk, Oak Park, CA (US)

(73) Assignee: Envy Medical, Inc., Westlake Village, CA (US)

( * ) Notice: Subject to any disclaimer, the term of this patent is extended or adjusted under 35 U.S.C. 154(b) by 928 days.

(21) Appl. No.: 12/197,075

(22) Filed: Aug. 22, 2008

(65) Prior Publication Data

US 2010/0049210 A1 Feb. 25, 2010

(51) Int. Cl.
  *A61B 17/50* (2006.01)
  *A61B 17/54* (2006.01)
  A61B 17/32 (2006.01)

(52) U.S. Cl.
  CPC ... *A61B 17/545* (2013.01); *A61B 2017/320012* (2013.01)
  USPC ........................................ 606/131

(58) Field of Classification Search
  CPC ................. A61B 17/545; A61B 2017/320004; A61B 2017/00761; A61B 2017/320012; A61B 2217/005; A61B 2217/007; A61M 1/0058; A61M 27/00
  USPC .......... 606/127, 128, 131–133; 604/289, 290, 604/313; 30/123.45; 451/344, 356, 659; 206/438, 471, 564
  See application file for complete search history.

(56) References Cited

U.S. PATENT DOCUMENTS

| | | | | |
|---|---|---|---|---|
| 6,846,218 | B2 * | 1/2005 | Kermode et al. | 450/37 |
| 2001/0023351 | A1 * | 9/2001 | Eilers et al. | 606/131 |
| 2002/0133176 | A1 | 9/2002 | Parkin et al. | |
| 2002/0169461 | A1 * | 11/2002 | Simon et al. | 606/131 |
| 2002/0183702 | A1 * | 12/2002 | Henley et al. | 604/305 |
| 2003/0097139 | A1 * | 5/2003 | Karasiuk | 606/131 |
| 2005/0277950 | A1 * | 12/2005 | Pilcher et al. | 606/131 |
| 2006/0086634 | A1 * | 4/2006 | Steppe | 206/438 |
| 2006/0129140 | A1 * | 6/2006 | Todd et al. | 606/1 |
| 2006/0161178 | A1 | 7/2006 | Lee | |
| 2007/0156124 | A1 | 7/2007 | Ignon et al. | |
| 2007/0265586 | A1 * | 11/2007 | Joshi et al. | 604/313 |
| 2010/0030132 | A1 * | 2/2010 | Niezgoda et al. | 604/22 |

FOREIGN PATENT DOCUMENTS

WO  WO 2004082469 A2 *  9/2004

OTHER PUBLICATIONS

International Search Report mailed Apr. 14, 2010 from International application PCT/US2009/054797 filed Aug. 24, 2009, 3 pages.

\* cited by examiner

*Primary Examiner* — Katherine M Shi

(74) *Attorney, Agent, or Firm* — Aka Chan LLP

(57) ABSTRACT

A microdermabrasion system upgrade kit includes a plurality of couplers from which a user may choose one or more couplers in order to connect the upgrade kit to a vacuum source of an existing microdermabrasion system. In an implementation, the upgrade kit includes a power socket that the user can plug the vacuum source into.

28 Claims, 18 Drawing Sheets

MICRODERMABRASION SYSTEM UPGRADE KIT

BACKGROUND OF THE INVENTION

The invention relates to the field of devices to treat human skin and more specifically to an upgrade kit which can be used to upgrade an existing microdermabrasion system.

As people age, they look for ways to maintain a youthful appearance. Some invasive cosmetic techniques include surgical approaches including eye lifts, face lifts, skin grafts, and breast lifts. However, these invasive techniques also have risks and potential complications. Some people have died during cosmetic surgery operations. Therefore, it is desirable to have noninvasive cosmetic techniques.

A noninvasive technique for obtaining a more youthful appearance is through microdermabrasion. Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone.

There is a continuing demand for microdermabrasion systems that are more effective at, for example, removing dead cells and nourishing the skin. There is also a continuing demand for systems that are easier and safer to use. In some cases a user may already have an existing microdermabrasion system. Although another microdermabrasion may offer additional benefits and features, the user may be reluctant to purchase a completely new system. Therefore, there is a need for improved systems and techniques for upgrading existing microdermabrasion systems.

BRIEF SUMMARY OF THE INVENTION

Techniques and devices are used to upgrade an existing microdermabrasion system (e.g., pimp your Peel™, a trademark of the assignee). A microdermabrasion system upgrade kit includes a plurality of couplers from which a user may choose one or more couplers in order to connect the upgrade kit to a vacuum source of an existing microdermabrasion system. In an implementation, the upgrade kit includes a power socket that the user can plug the vacuum source into.

In an embodiment, a microdermabrasion system upgrade kit includes a container, including a plurality of couplers, where a first and second coupler have a first end with the same coupler diameter, and a second end of the first coupler has a different diameter than a second end of the second coupler, a console including a power socket that outputs power; a first switch, connected to a supply line, a second switch, connected between the supply line and the power socket; and a security circuit, connected to the supply line and the second switch, and a microdermabrasion hand piece, connected to the console. The microdermabrasion hand piece includes an abrasive tip having an abrasive surface, at least one fluid output opening having an outer edge at a first position outside a periphery of the abrasive surface, and at least one fluid input opening having an outer edge at a second position outside a periphery of the abrasive surface, where the second position is a greater distance away from the abrasive surface than the first position.

The fluid input opening may connect to a first passageway, the fluid output opening may connect to a second passageway, and the first passageway may have a greater diameter than the second passageway.

In another embodiment, the fluid input opening connects to a first tubular passageway, the fluid output opening connects to a second tubular passageway, and the first and second tubular passageways share a common center axis. In another embodiment, the fluid input opening connects to a first tubular passageway, the fluid output opening connects to a second tubular passageway, and the second passageway is within the first passageway.

Fluid deposited on the abrasive tip from the one fluid output opening may be capable of being drawn into the one fluid input opening from at least two different directions, opposite of one another. Fluid deposited on the abrasive tip from the one fluid output opening may be capable of being drawn into the one fluid input opening from at least two different directions, transverse to one another.

In an embodiment, fluid deposited on the abrasive tip from the one fluid output opening is drawn into the one fluid input opening without passing through a porous material.

Fluid from the one fluid output opening may be placed on the abrasive surface without passing through the abrasive surface. The one fluid input opening may encircle the abrasive surface.

In an embodiment, a second fluid input opening has an outer edge at a third position outside a periphery of the abrasive surface, where the third position is a greater distance away from the abrasive surface than the first position, and the third position is on an opposite side of the abrasive surface from the second position.

In an embodiment a microdermabrasion system upgrade kit includes a container, including a plurality of couplers, where a first and second coupler have a first end with the same coupler diameter, and a second end of the first coupler has a different diameter than a second end of the second coupler, a console including a power socket that outputs power, a first switch, connected to a supply line, a second switch, connected between the supply line and the power socket, a security circuit, connected to the supply line and the second switch, and a vacuum tube input line having a diameter to fit the first ends of the first and second couplers, and a microdermabrasion hand piece, connected to the console and the vacuum tube input line.

In a further embodiment, an enclosure of the console does not include a vacuum pump. The container may include a base member, a reclosable lid, and a tray that fits in the base member, the tray having a first cavity to hold the first coupler and a second cavity to hold the second coupler.

In the tray, adjacent to the first cavity may be a first label and adjacent to the second cavity may be a second label, different from the first label.

The kit may include an instruction manual and video disc, where the video disc has a video presentation showing how to connect the console to a vacuum pump external to the console.

In an embodiment, a microdermabrasion system upgrade kit includes a container, including a plurality of couplers, where a first and second coupler have a first end with the same coupler diameter, and a second end of the first coupler has a different diameter than a second end of the second coupler, a console including a power socket that outputs power, a first switch, connected to a supply line, a second switch, connected between the supply line and the power socket, and a security circuit, connected to the supply line and the second switch, where an enclosure of the console does not include a vacuum pump, and a microdermabrasion hand piece, connected to the console.

Turning on the first switch may turn on a vacuum pump pressure display of the console and the power socket. The enclosure may have dimensions which are insufficient for housing a vacuum pump. The enclosure may not have a forced air output vent that is connected to the hand piece.

The kit may further include an instruction manual and video disc, where the video disc has a video presentation showing how to connect the console to a vacuum pump external to the console.

Other objects, features, and advantages of the present invention will become apparent upon consideration of the following detailed description and the accompanying drawings, in which like reference designations represent like features throughout the figures.

DETAILED DESCRIPTION OF THE INVENTION

This patent application incorporates by reference U.S. patent application 12/197,065; U.S. patent application 12/197,047; U.S. patent application Ser. No. 29/304,428, filed Feb. 29, 2008; U.S. patent application Ser. No. 29/322, 102, filed Jul. 29, 2008; U.S. patent application Ser. No. 29/322,106, filed Jul. 29, 2008; U.S. patent application Ser. No. 12/040,867, filed Feb. 29, 2008; U.S. patent application Ser. No. 10/393,682, filed Mar. 19, 2003; and U.S. Pat. No. 6,695,853, filed Nov. 21, 2001, and issued Feb. 24, 2004.

Figure 1:
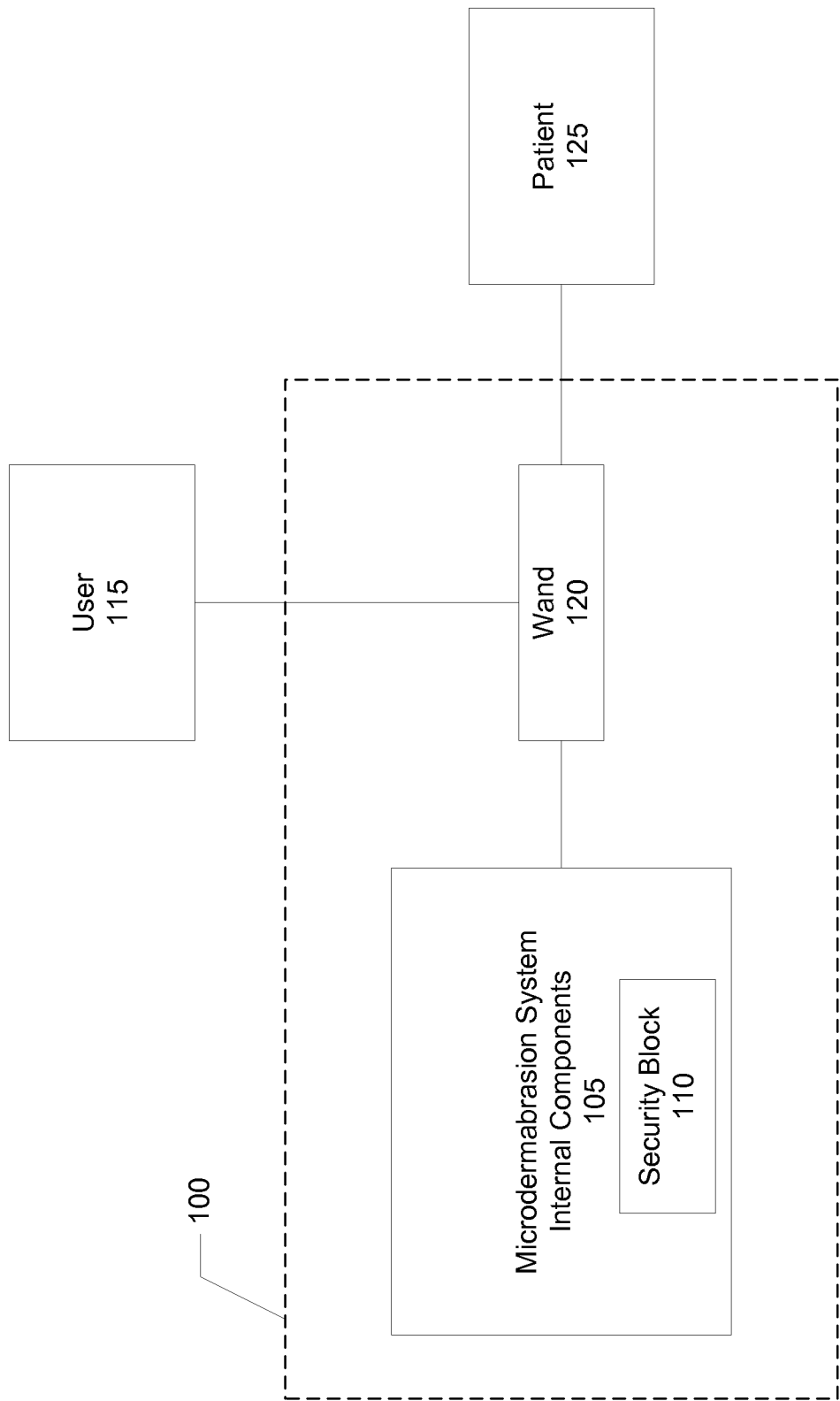
FIG. 1 shows block diagram of a microdermabrasion system according to the present invention.

FIG. 1 is a simplified block diagram of a microdermabrasion or dermabrasion system 100. The system has internal components 105 including a security block 110 that controls a security feature of the system. During a microdermabrasion treatment, a user 115 holds a wand or hand piece 120 and runs the wand over a patient's 125 skin to exfoliate it. The user may be a doctor, technician, operator, or aesthetician. After treatment, the patient leaves with a more youthful and healthful appearance.

Figure 2:
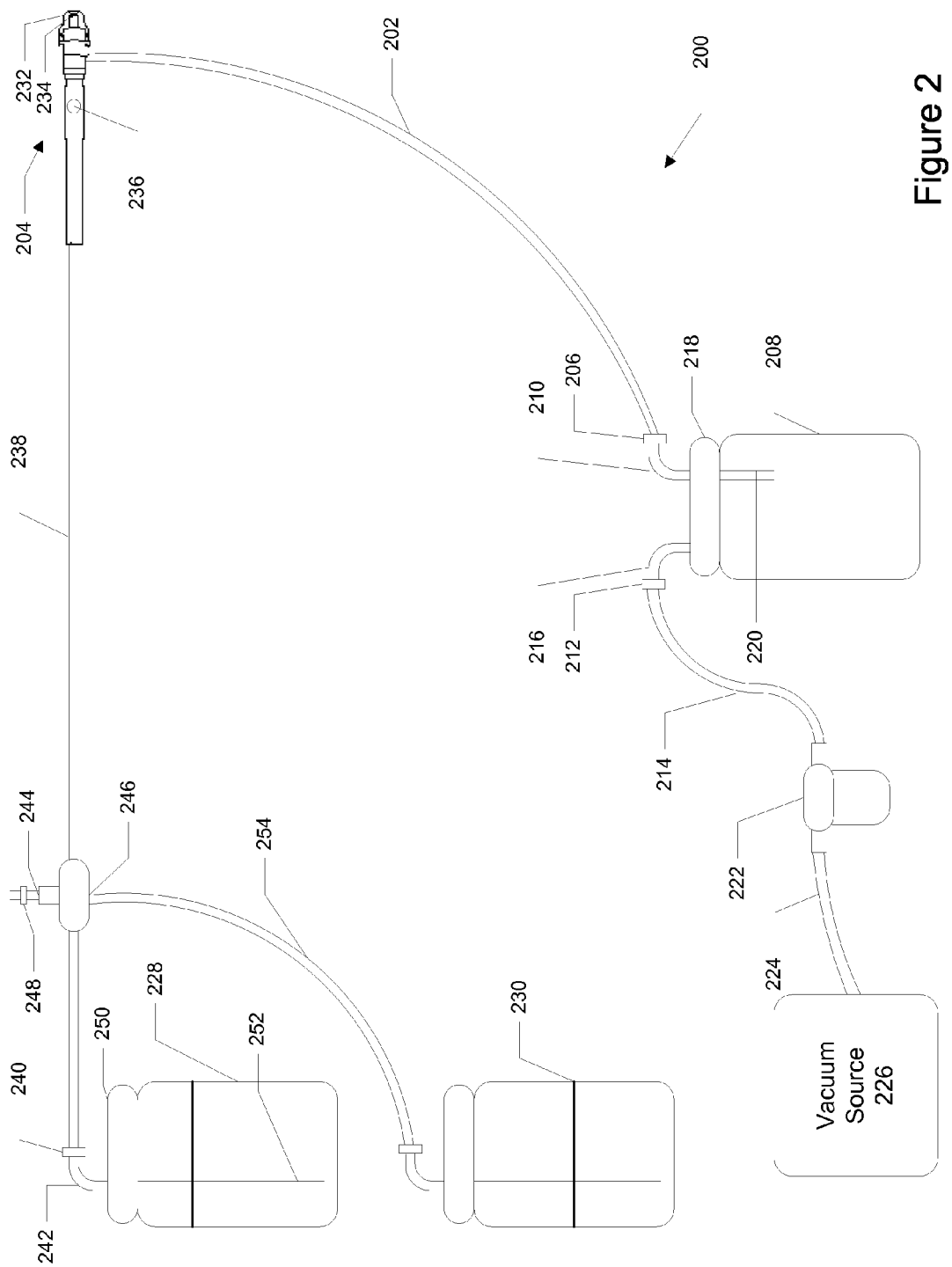
FIG. 2 shows an illustration of a microdermabrasion system without the security mechanism.

FIG. 2 shows an overview of the flow of a microdermabrasion system 200. A vacuum line 202 is connected to a wand or hand piece 204. Vacuum line 202 connects to an input 206 to a collection reservoir 208 via an elbow 210, for example. An output 212 connects with a second vacuum line 214 via an elbow 216, for example. A manifold cover 218 seals the input (206, 210) and output (212, 216) connections with collection reservoir 208 which is typically a jar made of glass or plastic, for example. An extension tube 220 connects with inputs 210 and 206 and extends into the collection reservoir. The collection reservoir holds the waste materials (e.g., abraded skin particles and, optionally, fluids) from the microdermabrasion process.

Optionally, a filter 222 may be provided between second vacuum line 214 and a third vacuum line 224 which connects to a vacuum source 226. Filter 222 ensures that no fluid, skin particles, abrasive particles, or other materials collected by collection reservoir 208 are transported to vacuum source 226.

Any type of filter may be used. For example, in a specific embodiment, filter 222 is an in-line condensation or hydrophobic filter, such as a water condenser produced by Wilkerson Labs and available as part number F0001-000 from Nor-Cal Controls, Incorporated of San Jose, Calif.

Vacuum source 226 may be any type of vacuum source such as a vacuum pump, an ejector (e.g., single-stage ejector and multi-stage ejector), or a vacuum blower. In an implementation, the vacuum source creates negative pressure compared to the pressure at the hand piece tip, so that there is suction at the tip (i.e., there is a pressure difference between the pressure at the vacuum source and tip). Because of this suction or negative pressure, air, fluid, particles, and other matter at the tip are drawn to the vacuum source (through the collection reservoir). Further, in an implementation, the negative pressure also draws fluid out of a first fluid reservoir 228, a second fluid reservoir 230, or both to the tip, where is it pulled back into the collection reservoir. The suction is a fluid path that can conduct any fluid, including liquids or gases.

Some examples of vacuum sources include the ProPeel, MDPeel, or iPeel, microdermabrasion systems available from eMed, Incorporated, Westlake Village, Calif. Vacuum source 226 may generate a vacuum pressure from about 2 pounds per square inch to about 14 pounds per square inch. For example, the vacuum pressure may be about 3, 4, 5, 6, 7, 8, 9, 10, 11, 12, 13, or more than 14 pounds per square inch. In some embodiments, the vacuum pressure may be less than 2 pounds per square inch.

Vacuum source 226 may include a vacuum pressure adjustment control so that a user can vary the vacuum pressure. In a specific embodiment, the vacuum pressure adjustment control is a knob that can be rotated to change the vacuum pressure. In other embodiments, the vacuum pressure adjustment control is one or more push buttons, a slider bar, or other. A vacuum pressure gauge may indicate the current vacuum pressure. In a specific embodiment, the vacuum pressure gauge is a digital gauge. In another embodiment, the vacuum pressure gauge is a dial gauge.

In a specific embodiment, vacuum source 226 includes a fluid flow adjustment control so that a user can vary the fluid flow settings. The fluid flow may range from about 0 milliliters per minute to about 140 milliliters per minute. For example, the fluid flow may be about 10, 20, 30, 40, 50, 60, 70, 80, 90, 100, 110, 120, 130 milliliters, or more than 140 milliliters per minute. In a specific embodiment, the fluid adjustment control is a knob that can be rotated to change the fluid flow. In other embodiments, the vacuum pressure adjustment control is one or more push buttons, a slider bar, or other. A fluid flow gauge may indicate the current flow rate. In a specific embodiment, the fluid flow gauge is a digital gauge. In another embodiment, the fluid flow gauge is a dial gauge.

Wand 204 includes a tip holder 232 which holds a tip 234. A first fluid delivery line 238 extends from wand 204 and connects to an output 240 of first fluid reservoir 228 via an elbow 242, for example.

A breather line 244 may be connected in-line via a joint 246, for example, or other interconnection, and includes an adjustable valve 248 or other means for varying an amount of air that is allowed into first fluid delivery line 238. This feature allows, for example, the amount of vacuum pressure to be adjusted for a given fluid and allows fluids having different viscosities to be applied at the same vacuum pressure level, since different viscosities will require varying amounts of air to be introduced into breather line 244 to produce a constant vacuum pressure level.

Alternatively, a breather line or input with adjustment valve may be located on elbow 242 or directly on a manifold cover 250. Still further, a valve or other flow control mechanism 236 may be provided on wand 204 or in first fluid delivery line 238 to control the amount of fluid passing through the line. This feature can be provided alternatively, or in addition to breather line 248 discussed above.

The flow control mechanism or valve allows, for example, the user to turn off the flow of fluid to the wand so that the user can clean or replace the tip if it becomes clogged. The fluid flow control mechanism may be located on the wand as shown in FIG. 2 or anywhere along the fluid flow path such as on first fluid delivery line 238. Generally, however, the fluid flow control valve will be located on the wand or near the wand so that the user can quickly turn off the flow of fluid.

An input may be provided in manifold cover 250 which may be open to the atmosphere to prevent vacuum buildup in first fluid reservoir 228. Manifold cover 250 seals output (240, 242) connections with first fluid reservoir 228 which is typically a jar made of glass or plastic, for example, and contains lotions, vitamins, other skin treatment fluids, or combinations of these to be applied to the skin by wand 204. An extension tube 252 connects with output 240, 242 and extends into the first fluid reservoir to near the bottom of the first fluid reservoir to ensure that most all of the contents of the fluid reservoir are capable of being delivered through the system.

In a specific embodiment, second fluid reservoir 230 is also included. A second fluid delivery line 254 connects the second fluid reservoir to joint 246. Joint 246 may further include a valve to block or to permit the flow of fluid from the second fluid reservoir into first fluid delivery line 238.

The first fluid reservoir may include contents that are the same or different from the first fluid reservoir. For example, the first fluid reservoir may include topical anesthetics and the second fluid reservoir may include disinfectants. In various implementations, there are any numbers of fluid reservoirs. For example, an implementation may have more than two fluid reservoirs, such as three, four, five, six, seven, or more than seven fluid reservoirs.

Having more than one fluid reservoir allows, for example, different types of fluids to be used to treat different types of skin conditions that the patient may have without requiring the user to constantly remove the existing fluid reservoir and replace it with a new fluid reservoir that contains the appropriate fluid. For example, a patient with oily skin may require a different treatment regime than a patient with dry skin. The patient with the oily skin may thus be treated with fluid from the first fluid reservoir in which the fluid does not contain any oil-based products because such oil-based products may worsen the patient's skin condition. The patient with the dry skin may instead be treated with fluid from the second reservoir in which the fluid may include oil-based products to help moisturize the skin.

Abrasive particles, such as corundum crystals, sodium bicarbonate particles or other abrasive particles, including those discussed in U.S. Pat. No. 5,971,999 (which is incorporated by reference), for example may be included in the fluid reservoirs for delivery through the system to perform a microdermabrading function. However, in the present invention, microdermabrasion is typically accomplished via a bristled tip, abrasive tip, or both. If used, the abrasive particles may be used together with any of the fluids mentioned above, with some other fluid carrier medium, such as those described in U.S. Pat. No. 5,971,999, for example, or both.

The fluid reservoirs may contain solution or a suspension for purposes other than abrasion or pure abrasiveness. The compositions used in the present invention can include a wide and diverse range of components. The *International Cosmetic Ingredient Dictionary and Handbook,* 12$^{th}$ edition, 2008, which is incorporated by reference, describes an extensive variety of cosmetic and pharmaceutical ingredients commonly used in the skin care industry, which are suitable for use in the compositions of the present invention.

General examples, types or categories, or both, of compounds that may be employed include: bleaching formulations (e.g., 2 percent to 4 percent hydroquinone, 2 percent kojic acid, 1 percent vitamin K, and 1 percent hydrocortisone in an aqueous base); acne treatment formulations (e.g., salicylic acid, alcohol base buffered by witch hazel, etc.); fine lines/wrinkle treatment formulations (e.g., hyaluronic acid in an aqueous base); hydrating formulations (e.g., calendula, vitamins A, D, E, or other vitamins, or combinations of these in a mineral oil base); antioxidant formulations; free radical scavengers (e.g., vitamins A, E, K, or other vitamins, or combinations of these in a mineral oil base); pH adjusters; sunscreen agents; tanning agents and accelerators; nonsteroidal anti-inflammatory actives (NSAIDS); antimicrobial and antifungal agents; moisturizers; lightening agents; humectants; numbing agents; retinol (e.g., 0.2 percent to about 0.6 percent concentration); and water, or combinations of these.

The solution or suspension may contain extracts such as those from plants, vegetables, trees, herbs, flowers, nuts, fruits, animals, or other organisms, or combinations of these. Such extracts may be used to help condition the skin, provide a relaxing aroma, or both.

The solution or suspension may also contain viscosity increasing or decreasing agents, colorants, or combinations of these. In a specific implementation of the invention, the viscosity of the fluids used is about 1 centipoise (e.g., about 0.5 to 1.5 centipoise). However, in other implementations, the viscosity may range from 0.1 centipoise to 100 centipoise. The viscosity may be, for example, 0.2, 0.3, 0.4, 0.5, 0.6, 0.7, 0.8, 0.9, 1, 1.1, 1.2, 1.3, 1.4, 1.5, 1.6, 10, 20, 30, 40, 50, 60, 70, 80, 90, or more than 100 centipoise. In other applications the viscosity may be less than 0.1 centipoise.

In a specific implementation, the fluids, abrasive particles, or both for the fluid reservoirs may be packaged as a concentrated solution, powder, solids, or combinations of these to be mixed, diluted, or both by the microdermabrasion system, user, or both.

Other examples of product categories that may be employed alone or in combination with other compounds include, antiseptics, disinfectants, astringents, cleansers, pore decongestants, balms, botanicals, collagen stimulators, herbs, microemulsifiers, oxygen delivery vehicles, proteins, serums, skin firming agents, toners, topical anesthetics, emulsions, ointments, gels, tyrosinase inhibitors, and other related product categories.

Individually named products that may be used (with associated benefit indicated parenthetically) include: Aloe Vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); hydroquinones (bleaching); lactic acids (peel); magnesium ascorbic phosphate (free radical scavenger, collagen stimulator, bleaching); niacin (vascular dilation); phospholipids (moisturization); potassium (toning, psoriasis), and salicylic acids (acne); and related products. Of course, any combination of such elements may be provided-even in connection with abrasive particles.

Any of the products listed may be used with the microdermabrasion treatment tips of the invention. For example, the groves of a tip may be used to conduct botanicals, Aloe Vera, or alpha hydroxy, to name a few examples, to a patient's skin. The channels through which fluid is delivered may be partially formed in tip 234 and partially formed in tip holder 232. When tip 234 and tip holder 232 are put together, the groves in each of these mate to form a complete channel opening.

As another example, coenzyme Q-10, glycolic acids, or vitamin E, to name a few examples, may be conducted through an opening, surrounded by bristles, to the skin of a patient. The opening may extend to a position closer to patient's skin through a cylindrical column, nipple, or other structure to achieve a similar purpose.

Note, however, the present system may be used by eliminating the fluid reservoirs altogether, where microdermabrasion is performed in a "dry state" and first fluid delivery line 238 is simply left open to atmosphere, with or without a filter or valve, or both, for adjusting the amount or flow rate of air that is allowed into the first fluid delivery line. Similarly, dry or externally lubricated vacuum massage of tissue may be accomplished by tip 234 having a smooth surface.

A feature of the invention is that the system delivers fluids directly to the patient's skin while simultaneously exfoliating the skin. In an embodiment, the system uses a variety of specially formulated solutions to provide, for example, treatment for hyperpigmentation, dehydration, acne, and photodamage. Patients receive the most benefit when fluids are used to treat their skin-specific conditions that have specifically been tested and approved for use with the system. These fluids also provide a consistent level of quality. Furthermore, these fluids are tested in the system to ensure that they do not clog the system.

Unapproved fluids may not have been tested and have an uncertain quality. They may fail certain quality standards. Unapproved fluids, for example, may not contain active ingredients, may contain an insufficient quantity of active ingredients, may contain entirely incorrect ingredients, may contain improper proportions of ingredients, or may even contain hazardous ingredients. A patient who receives unapproved fluids as part of their microdermabrasion treatment may suffer dangerous consequences to their health, such as unexpected side effects, rashes, allergic reactions, a worsening of their skin condition, or other problem. Unapproved fluids, because they have not been tested in the system, may also clog the system.

Figure 3:
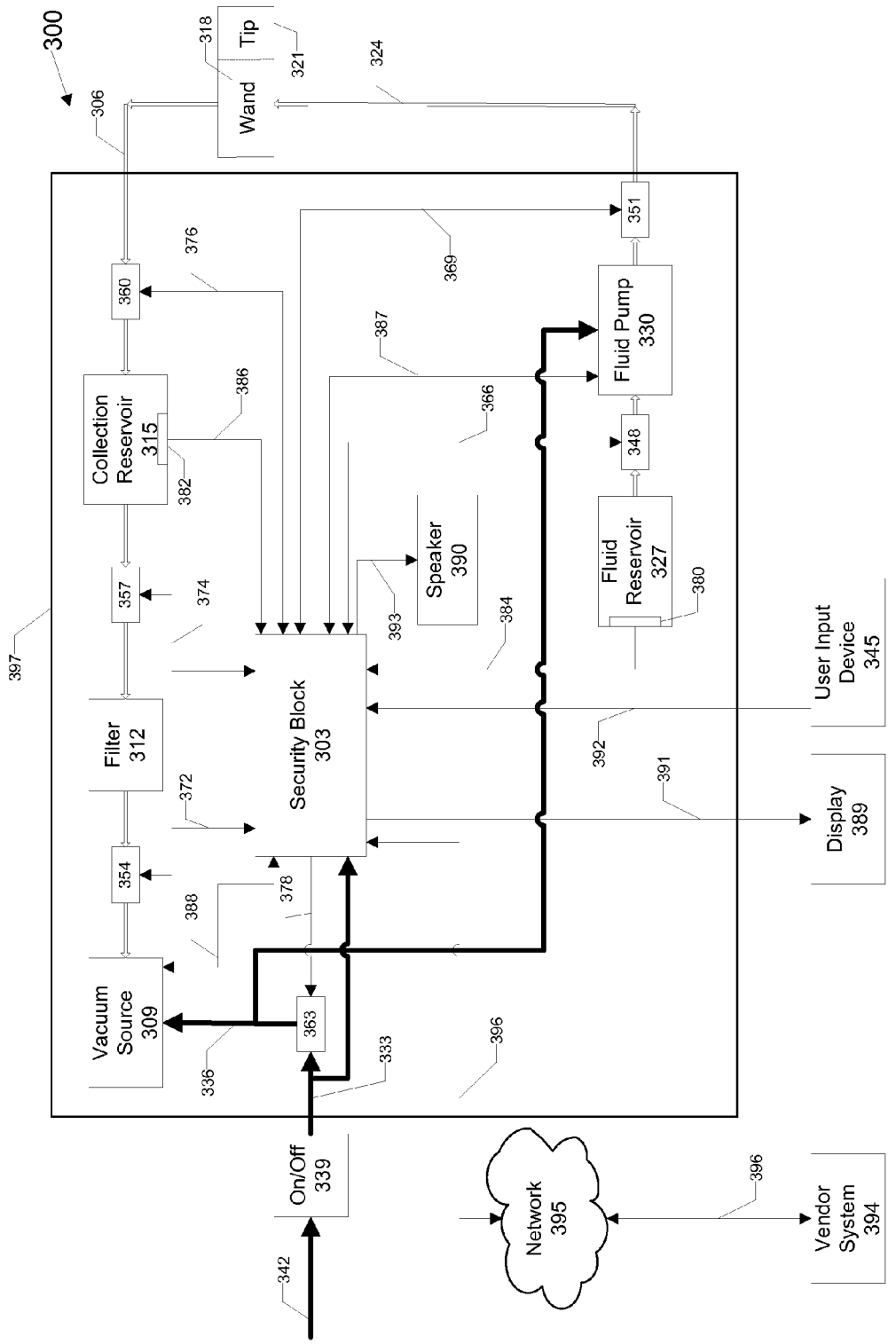
FIG. 3 shows a detailed block diagram of the microdermabrasion system with a security mechanism according to the present invention.

FIG. 3 shows a block diagram of a microdermabrasion system 300 which includes a security block 303 that controls operation of the system. The security block enables or disables operation of the microdermabrasion system based on certain input, which varies depending on the specific embodiment of the invention.

When operation is disabled by the security block, the user will not be able to operate the system. For example, the system will not turn on, fluid will not flow, there will be no vacuum, or power is not supplied to one or more components of the system. When enabled, the user will be able to operate the system normally.

The system has a vacuum path 306 that includes a vacuum source 309, which is connected to a filter 312, which is connected to a collection reservoir 315. Filter 312 may be optional and is not present in some implementations of the invention. Collection reservoir 315 is connected to a hand piece or wand 318 which has a tip 321.

The system has a fluid path 324 that that includes one or more fluid reservoirs such as a fluid reservoir 327, which is connected to a fluid pump 330, which is connected to wand 318. Fluid pump 330 may be optional and is not present in some implementations of the invention; in such a case, the fluid is drawn through fluid path 324, through hand piece 318, to collection reservoir 315 by vacuum source 309.

The system has a power path to distribute power (e.g., AC or DC, or both) to the components of the system. Power is supplied to the system through power input line 342 to an on-off switch 339. From on-off switch 339, power is supplied via a line 333 to security block 303. From on-off switch 339 and a switch 363, power is supplied via a line 336 to vacuum source 309 and fluid pump 330. When power is supplied as AC power (e.g., from an AC outlet), and a component such as security block 303 uses DC power, the system will include an AC-to-DC converter to convert AC power to DC power.

Security block 303 receives input from various sources such as a user input device 345 or other components of the system and generates a number of signals that goes to various components including vacuum source 309 and fluid pump 330. There are a number of valves 348, and 351 on fluid path 324. There are a number of valves 354, 357, and 360 on vacuum path 306. There is a switch 363 in line 333. Security block 303 generates signals that connect to these valves and switch 363.

The system includes one or more valves placed at various locations. In a specific implementation, there is at least one valve in vacuum path 306 or at least one valve in fluid path 324, or one valve in each of the vacuum and fluid paths. Each valve includes an input port, an output port, and a control signal input. Security block 303 generates a signal for each of the control signal inputs of the valves.

The control signal controls operation of a valve, so the valve is enabled or disabled. When enabled or open (e.g., control signal is a Boolean 1), the valve permits flow from its input port to its output port. When disabled or closed (e.g., control signal is a Boolean 0), the valve blocks flow from its input port to its output port.

The specific implementation in FIG. 3 has three valves 354, 357, and 360 in vacuum path 306 and two valves 348 and 351 in fluid path 324. Valve 348 is between fluid reservoir 327 and fluid pump 330 and has an input port connecting to fluid reservoir 327 and an output port connecting to fluid pump 330. In an implementation where fluid pump 330 is omitted, the output port connects directly to hand piece 318. A control signal 366 from security block 303 connects the control input of valve 348.

Valve 351 is between fluid pump 330 and wand 318 and has an input port connecting to fluid pump 330 and an output port connecting to wand 318. A control signal 369 from security block 303 connects the control input of valve 351.

Valve 354 is between filter 312 and vacuum source 309 and has an input port connecting to filter 312 and an output port connecting to vacuum source 309. A control signal 372 from the security block 303 connects the control input terminal of valve 354.

Valve 357 is between collection reservoir 315 and filter 312 and has an input port connecting to collection reservoir 315 and an output port connecting to filter 312. In an implementation where filter 312 is omitted, the output port connects directly to vacuum source 309. A control signal 374 from security block 303 connects the control input terminal of valve 357.

Valve 360 is between wand 318 and collection reservoir 315 and has an input port connecting to wand 318 and an output port connecting to collection reservoir 315. A control signal 376 from security block 303 connects the control input of valve 360.

Although FIG. 3 shows five valves, the specific number and position of the valves in a system of the invention may vary. As long as there is one valve in vacuum path 306, this valve can enable or disable the flow for this entire path. The position of this valve may be between vacuum source 309 and filter 312, between filter 312 and collection reservoir 315, or between collection reservoir 315 and hand piece 318. For example, when valve 360 is disabled or closed, there will be no vacuum to suck in or otherwise remove fluid, particulate, or other matter at hand piece 318.

By having more than one valve in vacuum path 306, this provides more points at which the path may be enabled or disabled. Further, between any two components (e.g., vacuum source and filter), there may be two or more valves, which would provide two or more points at which the flow for the path is enabled or disabled.

Similar to vacuum path 306, as long as there is one valve in fluid path 324, this valve can enable or disable the flow for this entire path. The position of this valve may be between fluid reservoir 327 and fluid pump 330 or between fluid pump 330 and hand piece 318. For example, when valve 351 is disabled or closed, the fluid in fluid reservoir 327 cannot flow to hand piece 318.

By having more than one valve in fluid path 324, this provides more points at which the path may be enabled or disabled. Further, between any two components (e.g., fluid reservoir and fluid pump), there may be two or more valves, which would provide two or more points at which the flow for the path is enabled or disabled.

Therefore, the system may include a total of five valves as shown. In other implementations, the system may include a total of only one valve, in either the vacuum or fluid path. The system may be two, three, four valves, or greater than five valves. For example, there may be six, seven, eight, nine, ten, eleven, twelve, thirteen, fourteen, fifteen, sixteen, or more than sixteen valves.

Furthermore, in a specific implementation of the invention, there are no valves in either the vacuum or fluid paths. In this implementation (discussed further below), enabling or disabling operation of the system will not be by way of blocking the vacuum or fluid paths, but rather another means such as disconnecting power to a component like vacuum source 309.

Specifically, in an implementation, the system includes one or more switches in the power path placed at various locations. In a specific implementation, there is at least one switch (e.g., switch 363) on the power path which is controlled by a control signal input. The security block generates a control signal 378 for the control signal input to switch 363.

Control signal 378 for the switch 363 opens or closes the switch. When closed or enabled (e.g., control signal is a Boolean 1), switch 363 permits power to flow from line 333 to line 336, connecting power to vacuum source 309 and fluid pump 330. When switch 363 is open or disabled (e.g., control signal is a Boolean 0), power is disconnected from the components and those components will not operate. Since security block 303 is connected to line 333, once on-off switch 339 is turned on, security block 303 receives power regardless of the setting for switch 363.

Switch 363 is between on-off switch 339 and vacuum source 309 and fluid pump 330. When switch 363 is enabled, power is distributed to both vacuum source 309 and fluid pump 330. When switch 363 is disabled, power is not distributed to both vacuum source 309 and fluid pump 330. Then vacuum source 309 and fluid pump 330 will not function, and operation of the system is disabled. The user can use wand 318, but there will be no vacuum and no fluid flow.

Although FIG. 3 shows only one switch with a line 336 connecting to both vacuum source 309 and fluid pump 330, other implementations may have different configurations. For example, there may be two switches, a first switch connecting line 333 to vacuum source 309 and a second switch connecting line 333 to fluid pump 330. Then, power can be selectively distributed to vacuum source 309 and fluid pump 330. Vacuum source 309 and fluid pump 330 can be turned on and off independently of each other. So, vacuum source 309 may be disabled or fluid pump 330 may be disabled.

A further configuration is only one component (e.g., vacuum source or fluid pump) is connected to line 336. Then when switch 363 is disabled, only that one component is disabled. This will effectively disable the system because there will be no vacuum or no fluid flow.

Further, there may be multiple switches in a power path to any of the components. As long as the power path to vacuum source 309 includes at least one switch connected to the security block, this switch can disable the system. For example, there may also be two, three, four, or more than five switches on the power path to vacuum source 309.

Having more than one switch on the power path to vacuum source 309 provides additional points at which the power may be disconnected from vacuum source 309. Additional switches and housing the switch in on-off switch 339 or vacuum source 309 may make it more difficult for a user to thwart the security block by installing a jumper wire around the switch.

Further, in an implementation, a component (e.g., vacuum source or fluid pump) has a control input (e.g., 387 or 388), which is connected to security block 303. This control input controls whether that component turns on or off, even when power is connected to the component. Then switch 363 is no longer needed, since security block 303 can control operation of the component directly.

In an implementation, security block 303 receives input (discussed further below) from an input device 345 and based on this input, the security block generates one or more signals that will enable or disable normal operation of the system. The security block receives and evaluates the input (e.g., authenticates the input), and makes a determination whether to permit normal operation. For normal operation, the user will be able use the microdermabrasion system to work on a patient. If normal operation is not enabled (e.g., may be called an exception condition or disabled condition), the microdermabrasion system will be disabled from operating in some way.

Further, when the system is disabled, the security block can cause a warning message to be displayed on a monitor or display 389 or an audible alert over a speaker 390 of the system, or both.

When normal operation is enabled, the security circuit can also monitor and control various system parameters. For example, the security circuit may disable the vacuum source if the collection reservoir is full so that the collection reservoir does not overflow.

When normal operation is enabled, the security circuit can also cause the display to show status messages on the system (such as amount of fluid in fluid reservoir or that the fluid collection reservoir is full), elapsed time the system has been on, or time remaining for use of a particular authorization code (see below). Further, when the system is operating, an alarm may sound when there is an error condition (e.g., fluid collection reservoir is full) or the authorization code entered into the system to enable normal operation has run out of time or "minutes" (see below).

In an implementation, the system operates as follows: A user inputs an authorization code to user input device 345, which is transmitted over a line 392 to security block 303. Then, security block 303 establishes a communication link 396 over a network 395 to a vendor system 394 and transmits the authorization code to vendor system 394. Vendor system 394 determines whether the authorization code is valid or invalid. Vendor system 394 then transmits its finding to security block 303.

If the authorization code is valid, security block 303 enables operation of the system. If the authorization code is invalid then security block 303 disables operation of the system.

In another implementation, the system operates as follows: user input device 345 is a card reader such as a magnetic swipe card reader, magnetic insertion card reader, optical scanner, smart card reader, barcode scanner, radio-frequency identification (RFID) reader, electrical interface, electrical connector, integrated circuit or chip, electrical connector for an integrated circuit, or the like, or a combination of these. In another implementation, user input device 345 is a memory reader (e.g., flash memory, USB reader). In yet another implementation, user input device 345 is a keypad or a microphone to accept a voice input.

Vendor system 394 is responsible for receiving information requests from security block 303, performing processing required to satisfy the requests, and for forwarding the results corresponding to the requests back to the requesting security block 303. The processing required to satisfy the request may be performed by vendor system 394 or may alternatively be delegated to other systems connection to network 395. Vendor system 394 may include a database system.

Figure 4:
FIG. 4 shows an illustration of an authorization code attached to a card in which an embodiment of the invention may be implemented.

FIG. 4 shows a specific implementation of an authorization code 405 that is encoded onto a magnetic strip of a card 410. Card 410 is packaged with a bottle or bottles of fluid. The card may include read-only memory areas, read-write memory areas, or both.

In other implementations, the authorization code may be printed as a bar code on the card, encoded onto a computer chip attached to the card, encoded onto a radio-frequency identification (RFID) tag attached to the card, printed using alphanumeric characters, printed using alphabetic characters, printed using numeric characters, or other, or combinations of these. The authorization code may be digital, binary, encrypted, or combinations of these. In a specific implementation where the authorization code is digital, the authorization code may include two or more bits, such as at least eight binary bits.

Only authorized fluids will include card 410. Unauthorized fluids will not include the card. Because authorization code 405 on card 410 is required to enable the system, users must purchase authorized fluids in order to use the system. This in turn ensures that patients are properly treated with authorized fluids.

Authorization code 405 permits the user to use the microdermabrasion system for a threshold number of times, time periods, or both. The threshold number of times varies. For example, where card 410 was included with a package containing twenty-four bottles of fluid, the threshold number may be twenty-four. Thus, the user would be permitted to use the microdermabrasion system twenty-four times because they purchased twenty-four bottles. As another example, card 410 may be included with one large bottle that is suitable for a certain number of treatments (e.g., five skin treatments). Thus, the threshold number would be five. The threshold number may range, for example, from about 1 to about 72. For example, the threshold number may be 2, 4, 6, 12, 18, 24, 36, 48, 72, or more than 72.

The threshold time period also varies. For example, a bottle of fluid may be intended for a 30-minute microdermabrasion treatment session. Thus, the threshold time period is 30 minutes. However, it may range, for example, from about 15 minutes to about 120 minutes. The threshold time period may be less than 15 minutes, 20, 25, 30, 35, 40, 45, 50, 60, 70, 80, 90, 100, 110, or more than 120 minutes. For example, where a bottle is intended for a 30-minute microdermabrasion session, security block 303 enables operation for 30 minutes. When 30 minutes have elapsed, security block 303 disables operation.

A specific flow example of security block 303 (see FIG. 3) using card 410 (see FIG. 4) is presented below. However, it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

1. The user purchases an authorized bottle or bottles of fluid which includes card 410.

2. The user places on-off switch 339 into the on position.

3. Power is supplied via line 333 to security block 303. Security block 303 disables operation of the system.

4. The user swipes card 410 through user input device 345. User input device 345 reads authorization code 405 on card 410 and transmits the authorization code to security block 303.

5. Security block 303 transmits the authorization code to vendor system 394.

6. Vendor system 394 determines whether the authorization code is valid. Vendor system 394 may use a number of different techniques to determine whether an authorization code is valid or invalid. In a specific implementation, the authorization codes are unique and can only be used a limited number of times. In this example, vendor system 394 maintains a list of authorization codes in a database table. A column of the database table includes a list of all the authorization codes generated. Another column of the database table includes a threshold number of times that the authorization code can be used. Another column includes the number of times that the authorization code has been used.

Vendor system 394 compares the user entered authorization code 405 with the list of authorization codes. If no match is found then authorization code 405 is invalid. This check prevents a user from creating their own authorization code.

If a match is found, then the vendor system checks the number of times that the authorization code has been used. In a specific implementation, the vendor system increments a counter variable that represents the number of times the authorization code has been used. If this number exceeds the threshold number then authorization code 405 is invalid. If this number does not exceed the threshold number then authorization code 405 is valid. In another implementation, the vendor system decrements a counter variable that represents the number of times the authorization code is allowed to be used. When this counter variable reaches zero, the authorization code is no longer valid because there are no more uses remaining on it. These checks prevent a user from continuously re-using authorization codes.

7. Vendor system 394 then responds to security block 303. If the response indicates that authorization code 405 is invalid, then security block 303 continues to disable operation of the system. Display 389 may include an error message such as, "Invalid authorization code. Please enter a different code."

However, if authorization code 405 is valid, then security block 303 enables operation of the system for a threshold period of time. After the threshold period of time, security block 303 disables the system. The user must then swipe card 410 through user input device 345.

Figure 5:
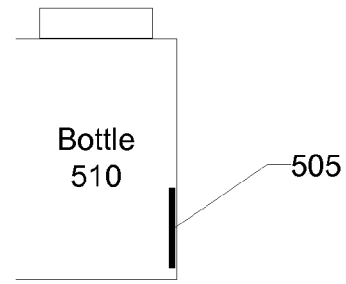
FIG. 5 shows an illustration of an authorization code attached to a bottle of fluid in which an embodiment of the invention may be implemented.

FIG. 5 shows another implementation where an authorization code 505 is attached to a bottle 510. In FIG. 5, authorization code 505 is encoded onto a chip (e.g., radio-frequency identification (RFID) tag), which is embedded in the label of a bottle. In other implementations, the authorization code may be printed as a bar code on a label of the bottle, encoded onto a magnetic strip attached to the bottle, or other, or combinations of these. In this specific implementation, the bottle is intended for a single microdermabrasion treatment. Thus, authorization code 505 is only valid for one use, for a threshold time period, or both. After the time expires, the system does not permit the user to re-enter the same authorization code.

Only authorized bottles of fluid will include authorization code 505. Unauthorized fluids will not include the authorization code. Because authorization code 505 on bottle 510 is required to enable the system, users must purchase authorized fluids for the system. This in turn ensures that patients are properly treated with authorized fluids.

The flow steps are similar to the flow steps for the implementation where the authorization code is included on a card. For example, a specific flow example of security block 303 (see FIG. 3) using authorization code 505 on bottle 510 (see FIG. 5) is presented below. However, it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

1. The user purchases an authorized bottle fluid.
2. The user places on-off switch 339 into the on position.
3. Power is supplied via line 333 to security block 303. Security block 303 disables operation of the system.
4. The user passes bottle 510 (e.g., having an RFID chip with a code) past user input device 345 so that the user input device (e.g., RFID reader) can read authorization code 505 on bottle 510. (In an alternate implementation, the user inserts into the machine a bottle having an embedded chip where a code is stored. The user input device—e.g., an electrical connector—interfaces with the embedded chip, so that the machine can read the code off the chip.) Then, user input device 345 transmits authorization code 505 to security block 303.
5. Security block 303 transmits authorization code 505 to vendor system 394.
6. Vendor system 394 determines whether the authorization code is valid using a similar process as that described above.
7. Vendor system 394 then responds to security block 303. If the response indicates that the authorization code is invalid, then security block 303 continues to disable operation of the system. Display 389 may include an error message such as, "Invalid authorization code. This bottle may have previously been used. Please discard the bottle and purchase a new bottle."

However, if authorization code 505 is valid, then security block 303 enables operation of the system for a threshold period of time. After the threshold period of time, security block 303 disables the system. Typically, the threshold period of time is the time required to empty bottle 510 during a microdermabrasion treatment session. The user must then use a new bottle.

Other implementations of a chip included on a card, bottle, or both are possible. For example, the chip may include writeable memory. User input device 345 then includes write capabilities in addition to read capabilities. Thus, each time the user swipes card 410 or passes bottle 510 through user input device 345, the user input device writes to the chip. For example, the user input device may increment a counter variable on the chip. When that counter variable exceeds a threshold number of uses stored on the chip, then security block 303 disables operation of the system. As another example, the user input device may decrement a counter variable on the chip. When the counter variable reaches zero, that indicates that there are no more uses remaining. The security block then disables operation of the system.

In yet another implementation, a chip (e.g., RFID chip) or code (e.g., bar code) is included with the bottle and is destroyed when the bottle is used. For example, the chip or code may be attached to or printed on a material which seals the bottle's opening. Some examples of materials include plastic, foil (e.g., aluminum foil), and paper. A user, prior to breaking the material, passes the bottle past user input device 345 which reads information (e.g., authorization code) stored on the chip or encoded onto the bar code. Based on the information that is read, the security block may enable operation of the system for a threshold period of time. In this implementation, the user, in order to use the fluid contained in the bottle, must break or puncture the material sealing the opening which in turn destroys the chip or bar code. Thus, while the bottle may be refilled with unauthorized fluids, the bottle will not be able to be used with the system because the chip or bar code will have been destroyed.

Thus, various implementations will not require the security block to connect to a network.

Figure 6:
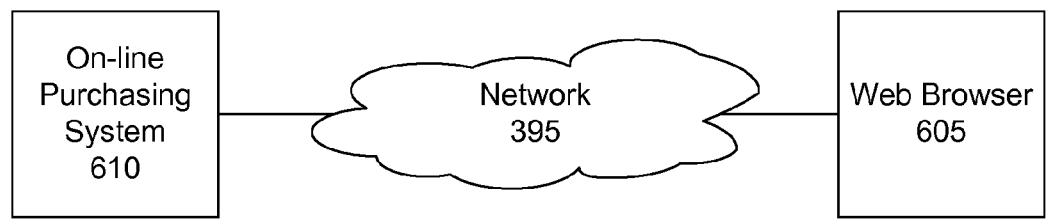
FIG. 6 shows a block diagram of a computer system and network in which an embodiment of the invention may be implemented.

FIG. 6 shows another implementation of the invention where the user purchases blocks of time for using the system. This use-based pricing offers several benefits. For example, it is economically efficient and fair because the system's cost is linked to its actual use. Thus, a user with a small number of patients to treat may incur lesser costs than a user with a large number of patients to treat. Use-based pricing may also lower the initial purchase cost of the system. Thus, more users are able to afford it. This in turn allows more patients to realize the benefits of having clean, healthy, and attractive skin.

A specific flow example for purchasing blocks of time is presented below, but it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

1. Using a Web browser 605, a user navigates to a vendor's on-line purchasing system 610.

2. The on-line purchasing system allows the user to enter the amount of time they would like to purchase. The purchase cost is based on a specific rate such as a dollar per hour rate (e.g., x dollars per hour).

3. The user enters the serial number for their microdermabrasion system. The serial number is a unique number that is associated with each microdermabrasion system. The serial number ensures that the particular block of time purchased is specific to a particular microdermabrasion system. In other implementations, the user may enter an identifier for the user or machine.

4. The user pays for their purchase using any electronic payment technology. This includes, for example, credit cards (e.g., Visa, Mastercard, American Express, Discover), debit cards, electronic checks, or other. In an implementation, the invention integrates with other third-party payment processing services such as Google Checkout, PayPal, PayPal Mobile, Pay with Skype, or others, or combinations of these.

5. Once the user has completed their payment the on-line purchasing system uses an encryption algorithm to generate an encrypted authorization code for the user to download. The encrypted authorization code is a unique code. It contains information such as the amount of time purchased and the serial number of the system for which time was purchased. For example, the code may be 80020080808168123, where a first field (the first three digits) gives the number of minutes purchased, a second field (the next eight digits) give the serial number, and a third field (the next six digits) gives a unique number code, so the machine can authenticate the authorization. Other fields can include time of day, month, year, or any other codes. The code may have any number of digits.

6. The user downloads the encrypted authorization code onto any portable memory device such as a universal serial bus (USB) drive.

7. The user inserts the portable memory device into the user input device. The user input device reads the encrypted authorization code and transmits it to the security block. In another implementation, the portable memory device is capable of wireless transmission (e.g., radio frequency (RF), infrared). In this case, the authorization code may be wirelessly transmitted to the user input device. This saves the user the step of manually placing the portable memory device into the user input device.

8. The security block then uses a decryption algorithm to decrypt the encrypted authorization code. In this implementation, the security block does not connect to the network.

9. When the encrypted authorization code is decrypted, the security block checks whether the authorization code is valid or invalid. This may involve several checks. For example, the security block checks that the serial number in the authorization code matches the serial number for the system. This prevents the user from reusing the authorization codes on a different system. If the serial numbers do not match, then the authorization code is invalid. Display 389 displays an error message such as, "Invalid authorization code. This authorization code is intended for a different microdermabrasion system. Please enter a different authorization code."

10. If the serial numbers match, then the security block does a further check to determine if that authorization code was previously used. The security block stores in memory a list of previously used authorization codes.

11. If the authorization code was not previously used, then the security block enables operation of the system. The security block stores in memory the amount of time the user purchased. The security block then tracks the amount of time that the system is enabled. When the time exceeds the amount of time purchased, then the security block disables the system.

12. If the authorization code was previously used, then the security block does a further check to determine whether there is any time remaining for that authorization code.

13. If there is a time balance remaining, then the security block enables operation of the system for that remaining time balance.

14. If there is no time balance remaining, then the security block continues to disable operation of the system. A message on display 389 states, for example, "There is no time remaining on this authorization code."

Any encryption algorithm may be used to produce a seemingly random authorization code. An example of a simplistic encryption algorithm is to increment each digit of the serial number by one, append the purchased time block, and append the date and time that the purchase was made. For example, if the serial number of the microdermabrasion system was 4283 and the user purchased a 60-minute time block on Mar. 1, 2007 at 0700 hours, then the encryption algorithm produces the authorization number 5394600301200080700.

The first four digits of the authorization number ("5 3 9 4") results from adding 1 to each of the digits of the serial number for the microdermabrasion system. The next two digits ("6 0") represents the time in minutes that the user purchased. The next two digits ("0 3") represents the month (March) in which the purchase was made. The next two digits ("0 1") represents the day of the month, while the last four digits ("2 0 0 8") represents the year. Finally, the last four digits ("0 7 0 0") represents the time that the purchase was made.

It will be clear to those skilled in the art that there are other encryption algorithms that may be used to produce the authorization code. These other encryption algorithms may include additional mathematical computations that decrement a number, apply a multiplication factor, or incorporate alphabetical characters, or other in order to produce a seemingly random authorization code. Examples of encryption algorithms include RSA, data encryption standard (DES), Triple-Des, Blowfish, International Data Encryption Algorithm (IDEA), Software-optimized Encryption Algorithm (SEAL), and RC4.

Other implementations of the encrypted authorization code are possible. For example, the on-line purchasing system, instead of generating an authorization code for the user to download, may instead generate an encrypted authorization code for the user to print, copy, or both. User input device 345 would then be a keypad for the user to manually enter the encrypted authorization code.

In a specific implementation, the system authorizes usage using one or more authentication factors. The authentication factor may be something the user has, something the user knows, or something the user does. For example, in a specific implementation, the system authorizes usage using two-factor authentication. A first authentication factor may be the card (i.e., something the user has) as discussed above and shown in FIG. 4. A second authentication factor may be something the user knows such as a personal identification number (PIN).

The user, in addition to swiping their card through the user input device, may also be required to enter a PIN. The security block may then transmit the PIN to the vendor system. The vendor system may determine whether the PIN is valid by, for example, comparing the entered PIN to a list of valid PINs. A user may be required to obtain a PIN from the vendor as part of a registration process after purchasing the microdermabrasion system.

As another example, the user may be required to call the vendor after purchasing a bottle of fluid in order to authenticate a key number that may be printed on the card or the bottle. For example, after purchasing a bottle of fluid, the user may be required to call the vendor and recite to the vendor (1) the key number and (2) information that identifies the microdermabrasion system in which the bottle will be used (e.g., serial number of the microdermabrasion system).

The vendor will then determine whether the key number is a valid key number. For example, the vendor may check whether the key number is included on a list of valid key numbers. If the vendor determines that the key number is not a valid key number then the vendor will inform the user that the key number is not valid. A key number may be invalid for any number of reasons. For example, the key number may have expired because it has already been used by that user or another user.

If the vendor determines that the key number is valid then the vendor may provide a PIN to the user. The PIN may be coded such that it will enable only that user's microdermabrasion system. For example, the PIN may include encrypted information that identifies the microdermabrasion system in which it can be used. This helps to prevent the user from reusing the PIN on different microdermabrasion systems.

The user, after obtaining the PIN, will then be required to both insert the card into the microdermabrasion system and enter the PIN. The security block will then determine whether the card and PIN are valid. For example, the security block may use a decryption algorithm to decrypt the PIN. The security block may then compare the decrypted PIN with, for example, the serial number of the microdermabrasion system to ensure that the user is not attempting to use the PIN on a different microdermabrasion system.

If there is a match then the security block will permit operation of the system by, for example, sending power to the microdermabrasion system components and opening valves. If there is not a match then the security block will block operation of the system by, for example, preventing power from reaching the microdermabrasion system components and closing valves.

The card may include information such as the amount of time, number of uses that the card is valid for, or both. Thus, the security block may track the amount of time remaining on the card, the number of uses remaining on the card, or both. When that time or number of uses expires then the security block will disable operation of the system.

For example, the card may include a writeable memory area so that the microdermabrasion system can write to the card and update the time or uses remaining on the card. As another example, the card may include a read-only memory area. The security block may then store in memory the amount of time or number of uses remaining on the card.

In another implementation, an authentication factor may include the internet protocol (IP) address of the microdermabrasion system. For example, after the user inserts the card that may be included with a bottle of fluid into the user input device, the security block may transmit the IP address of the microdermabrasion system to the vendor. The vendor may then create an association between that card and IP address. Thus, the next time that the card is used the vendor can determine whether the card being used on the same microdermabrasion system or whether the user is attempting to use the card on a different microdermabrasion system.

The vendor, after verifying the card and IP address, may then respond with an authorization message to the microdermabrasion system which enables the microdermabrasion system.

The vendor may track the usage of the microdermabrasion system. For example, information included on the card may include the amount of time, number of uses that the card is valid for, or both. Once that time or number of uses expires then the vendor will respond with a message to the microdermabrasion system which disables the system.

Figure 7:
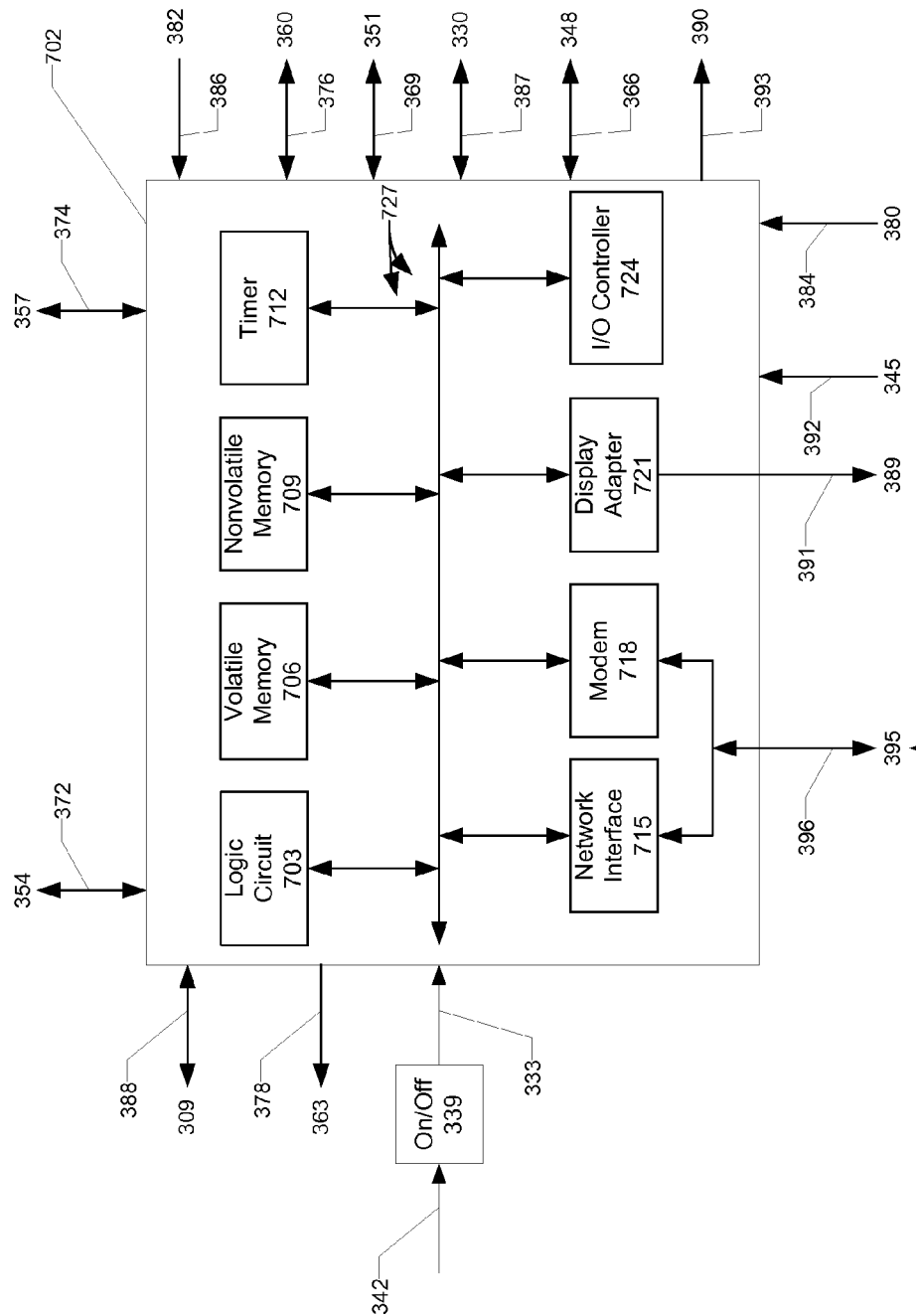
FIG. 7 shows a block diagram of a security block for the microdermabrasion system in which an embodiment of the invention may be implemented.

FIG. 7 shows more detailed block diagram of a specific implementation of a security block for a microdermabrasion system, such as security block 303 of FIG. 3. This security block 702 includes a logic circuit 703, a volatile memory 706, a nonvolatile memory 709, a timer 712, a network interface 715, a modem 718, a display adapter 721, and an input/output (I/O) controller 724, which are connected together by a bus 727. The invention may be also be used with security blocks with additional or fewer subsystems. For example, a security block could include more than one logic circuit or a system may include a cache memory.

Arrows such as 727 represent the system bus architecture of the security block. However, these arrows are illustrative of any interconnection scheme serving to link the subsystems. For example, modem 718 could be connected to the other subsystems through a port or have an internal direct connection to logic circuit 703. The logic circuit may be an ASIC such as a gate array, PLD, or FPGA. The logic circuit may be a processor or multiple processors or a multicore processor, which may permit parallel processing of information. This figure shows but one example of a security block configuration suitable for use with the present invention. Other configurations of subsystems suitable for use with the present invention will be readily apparent to one of ordinary skill in the art.

Volatile memory 706 may include random access memory (RAM), dynamic random access memory (DRAM), static random access memory (SRAM), and other similar media, and combinations of these. Volatile memory is memory that does not retain its stored information after power is removed.

Nonvolatile memory 709 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other solid-state storage (e.g., USB flash drive), battery-backed-up volatile memory, tape storage, reader, and other similar media, and combinations of these. Volatile memory is memory that retains its stored information even after power is removed.

In a specific implementation, timer 712 is used to track the amount of time that the system is in operation. This allows the security block to disable operation of the system when a threshold time is reached (see above discussion).

Code to implement the invention may be referred to as software or firmware (e.g., which is typically stored in persistent memory such as a ROM or flash memory). A computer-implemented or computer-executable version of the invention may be embodied using, stored on, or associated with computer-readable medium. A computer-readable medium may include any medium that participates in providing instructions to one or more logic circuits for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on nonvolatile memory 709. The source code of the software of the present invention may also be stored or reside on nonvolatile memory 709 (e.g., hard disk, magnetic disk, tape, or CD-ROM). As a further example, code of the invention may be transmitted via wires, radio waves, or through a network such as the Internet.

An implementation of the invention uses software to control various components such as the vacuum source 309, fluid pump 330, or both. Data line 388 connects the security block to the vacuum source 309. Data line 387 connects the security block to the fluid pump 330.

The software or firmware may control, for example, the rate at which fluid is pumped from the fluid pump 330, the vacuum pressure generated by the vacuum source 309, and other variables.

Network 395 may itself be comprised of many interconnected computer systems and communication links. Communication link 396 may be hardwire links, optical links, satellite or other wireless communications links, wave propagation links, or any other mechanisms for communication of information. Various communication protocols may be used to facilitate communication between security block 702 and other systems. These communication protocols may include TCP/IP, HTTP protocols, wireless application protocol (WAP), vendor-specific protocols, customized protocols, and others. While in one embodiment, network 395 is the Internet, in other embodiments, network 395 may be any suitable communication network including a local area network (LAN), a wide area network (WAN), a wireless network, a intranet, a private network, a public network, a switched network, and combinations of these, and the like.

Referring now to FIG. 3, an optional fluid pump 330 is used in some embodiments to assist in the delivery of fluids. Fluid pump 330 may include a fluid flow adjustment control so that a user may vary the fluid flow settings. The fluid flow may range from about 0 milliliters per minute to about 140 milliliters per minute. For example, the fluid flow may be about 10, 20, 30, 40, 50, 60, 70, 80, 90, 100, 110, 120, 130 milliliters, or more than 140 milliliters per minute. In a specific embodiment, the fluid adjustment control is a knob that can be rotated to change the fluid flow. In other embodiments, the adjustment control may be one or more push buttons, a slider bar, or other. A fluid flow gauge may indicate the current flow rate. In a specific embodiment, the fluid flow gauge is a digital gauge. In another embodiment, the fluid flow gauge is a dial gauge.

In a further embodiment, user input device 345 includes a control to allow the user to choose which fluid reservoir to draw fluid from when, for example, there is more than one fluid reservoir.

In a further embodiment, the system includes one or more fluid property sensors (e.g., surface acoustic wave sensor). The fluid property sensors are placed at any location in which they will measure the properties of the fluid. For example, fluid property sensors may be placed anywhere along fluid flow path 324, on collection reservoir 315, on fluid reservoir 327, in fluid pump 330, in hand piece 318, or combinations of these.

The fluid property sensor generates a signal that is sent to security block 303. The signal may indicate whether or not the fluid properties meet a certain criteria, contain the proper ingredients, or both. Depending on the signal, security block 303 may disable the system by, for example, disconnecting power to vacuum source 309 and closing valves.

The specific implementation in FIG. 3 has two fluid property sensors 380 and 382. Fluid property sensor 380 is located inside fluid reservoir 327. Fluid property sensor 380 is attached to extension tube 252 (see FIG. 2). A signal 384 is generated by fluid property sensor 380 and sent to security block 303.

Fluid property sensor 382 is located inside collection reservoir 315. Fluid property sensor 382 is attached to extension tube 220 (see FIG. 2). A signal 386 is generated by fluid property sensor 382 and sent to security block 303.

The fluid property sensors send a signal (e.g., signal is a Boolean 1) when they detect, for example, a fluid viscosity that is greater than a threshold value and a signal (e.g., signal is a Boolean 0) when they detect, for example, a fluid viscosity that is less than or equal to a threshold value.

The threshold value for the viscosity may vary. For example, the threshold value is typically about 1 centipoise (e.g., about 0.5 to 1.5 centipoise). However, in other implementations, the threshold value may range from 0.1 centipoise to 100 centipoise. The threshold value may be, for example, 0.2, 0.3, 0.4, 0.5, 0.6, 0.7, 0.8, 0.9, 1, 1.1, 1.2, 1.3, 1.4, 1.5, 1.6, 10, 20, 30, 40, 50, 60, 70, 80, 90, or more than 100 centipoise. In other applications the threshold value may be less than 0.1 centipoise.

The fluid property sensors ensure that only fluids which meet a certain quality criteria are used in the system. For example, vacuum source 309 may not be able to vacuum fluids having too high of a viscosity. In other implementations of the invention, other fluid properties in addition to or in lieu of viscosity may be measured. For example, these properties may include the temperature or density of the fluid. It may also include whether or not certain chemicals are present or are not present.

The type of valves 348, 351, 354, 357, and 360 may vary. For example, the valves may be ball valves, butterfly valves, choke valves, check valves, diaphragm valves, gate valves, globe valves, knife valves, needle valves, piston valves, pinch valves, plug valves, y-valves, or other, or combinations of these.

The valves may be controlled by actuators. For example, the actuators may be eletromechanical actuators (e.g., electric motor, solenoid). The actuators may be pneumatic actuators, or hydraulic actuators.

In a specific implementation, one or more valves may include devices such as flowmeters to measure flow rates (e.g., volumetric flow rate, mass flow rate). The flow rates may be communicated to security block 303. In another implementation, such devices to measure flow rates (e.g., flowmeters) are separate from the valves. A specific embodiment may have both valves and flowmeters. For example, there may be a valve between fluid reservoir 327 and fluid pump 330; a flowmeter and a valve between fluid pump 330 and hand piece 318; a flowmeter between hand piece 318 and collection reservoir 315; and a valve between vacuum source 309 and filter 312.

Measuring the flow rates provides, for example, a way for users to pay for the system based on use. It also provides a way for the system to disable the system based on the amount of fluid used.

There may be any number of flow meters. For example, there may be zero, one, two, three, four, five, six, seven, eight, nine, ten, or more than ten flowmeters. Having multiple flowmeters provides, for example, a way to determine if an optimum flow rate is being achieved. For example, a flowmeter may be placed on vacuum path 306 and on fluid path 324. The difference between the two flowmeters is an indication of how much fluid is left on the patient's skin. Too little fluid may not provide enough lubrication and cause the patient discomfort. Too much fluid may provide excess lubrication that inhibits the skin abrading particles of tip 321.

In a specific implementation, one or more electric meters may be included on the power path. For example, an electric meter may be included on line 336 between the vacuum source and switch 363. The electric meter may be connected to the security block via a data line. The electric meter may be, for example, a kilowatt hour meter, joule meter, electromechanical meter, electronic meter, or a solid state meter.

The electric meter may be used, for example, to measure the electrical energy consumed by the vacuum source, fluid pump, or both. Measuring the electricity consumption provides, for example, a way for users to pay for the system based on use. It also provides a way for the system to disable the system based on the amount of electrical energy consumed.

In a specific embodiment, on-off switch 339 is a toggle switch. In other embodiments, the on-off switch may instead be one or more push buttons (e.g., on button, off button), rotary switch, key switch, foot switch, rocker switch, or other type of switch.

Switch 363 may be, for example, a circuit, an analog switch, a contactless switch, and the like.

In the implementation shown in FIG. 3, the system includes a display 389 which is connected to security block 303 via data line 391. A speaker 390 is also included. Speaker 390 is connected to security block 303 via data line 393.

Display 389 may be a flat panel display such as a liquid crystal display (LCD), plasma display, thin film transistor liquid crystal display (TFT LCD), electroluminescent (EL), or organic light emitting diode (OLED) display. The screen may include a touch screen interface. Such touch screen interfaces are easier to clean if they become contaminated because they do not contain mechanical parts.

Display 389 is used to provide information such as messages to the user. Table A below shows several examples of messages that may be displayed.

TABLE A

| Message |
| --- |
| Improper authorization code entered. Please enter a new authorization code. |
| Your time has expired. Please purchase additional time. |
| You have x minutes remaining. |
| You have x uses remaining. |
| The fluid has an improper viscosity level and may not be approved for use with this system. Please replace the fluid with fluid from your authorized dealer. |
| The collection reservoir is full. The system has automatically shut off the vacuum pump so that the collection reservoir does not overflow. Please empty the collection reservoir. |

Display 389 may include one or more indicator lights (e.g., blinking lights, solid lights, and different color lights) to indicate, for example, whether the microdermabrasion system is ready for use or not ready for use. For example, a solid green colored light may indicate that the microdermabrasion system is ready to be used on a patient. A blinking red colored light may indicate that the microdermabrasion system is not ready for use. In an implementation, the indicator lights may be light emitting diodes (LEDs). In other implementations, another type of radiation source may be used either alone or in combination with the LEDs.

Speaker 390 may be used to provide audio alerts. For example, an improper authorization code may include an audible beep in addition to a message on display 389.

Portions of the microdermabrasion system may be housed in a case 397. In the implementation shown in FIG. 3, case 397 houses security block 303, switch 363, vacuum source 309, filter 312, speaker 390, fluid pump 330, sensors 380, 382, valves 348, 351, 354, 357, and 360, collection reservoir 315, and fluid reservoir 327. On-off switch 339, display 389, user input device 345, and hand piece 318 may be located outside the case.

In another implementation, fluid reservoir 327 and collection reservoir 315 are located outside of the case. This allows a user to quickly replace fluid reservoir 327 and empty collection reservoir 315.

Figure 8:
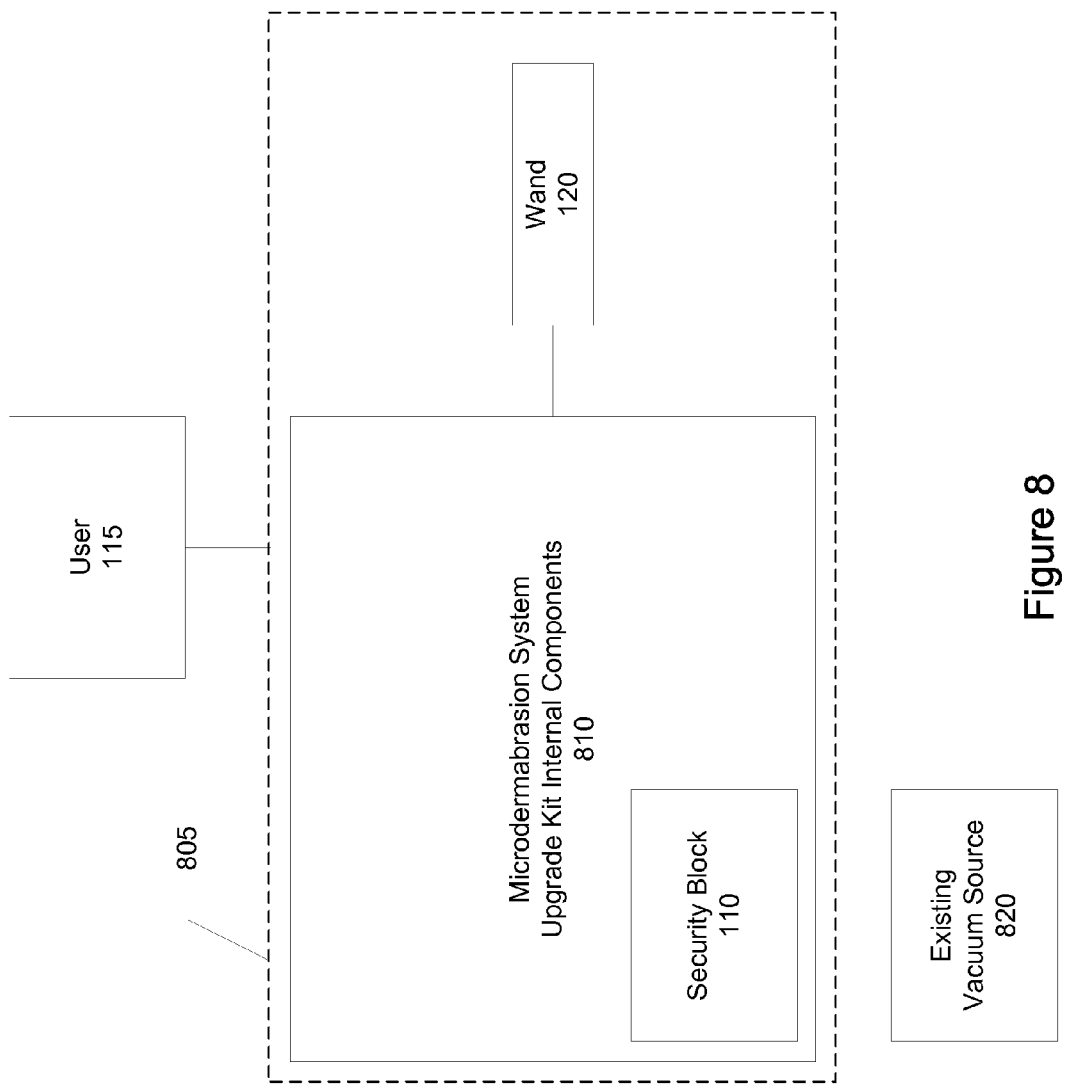
FIG. 8 shows a block diagram of a microdermabrasion upgrade kit in which an embodiment of the invention may be implemented.

FIG. 8 shows a block diagram of a specific implementation of a system of the invention. In this implementation, the security block is part of a microdermabrasion or dermabrasion upgrade kit 805. The upgrade kit has internal components 810 including security block 110 that controls the security feature of the system. However, in other implementations, the security block is not included with the upgrade kit. The upgrade kit may further include wand 120.

The upgrade kit allows user 115 to upgrade their existing microdermabrasion system by, for example, connecting an existing vacuum source 820 from their existing microdermabrasion system to the upgrade kit. Thus, in a specific implementation, the upgrade kit will not include a vacuum source. The upgrade kit provides an economical way for users and their patients to reap the benefits of the microdermabrasion system of the present invention. That is, users can reuse portions of their existing microdermabrasion system, such as their existing vacuum source, with the microdermabrasion system of the present invention.

Figure 9:
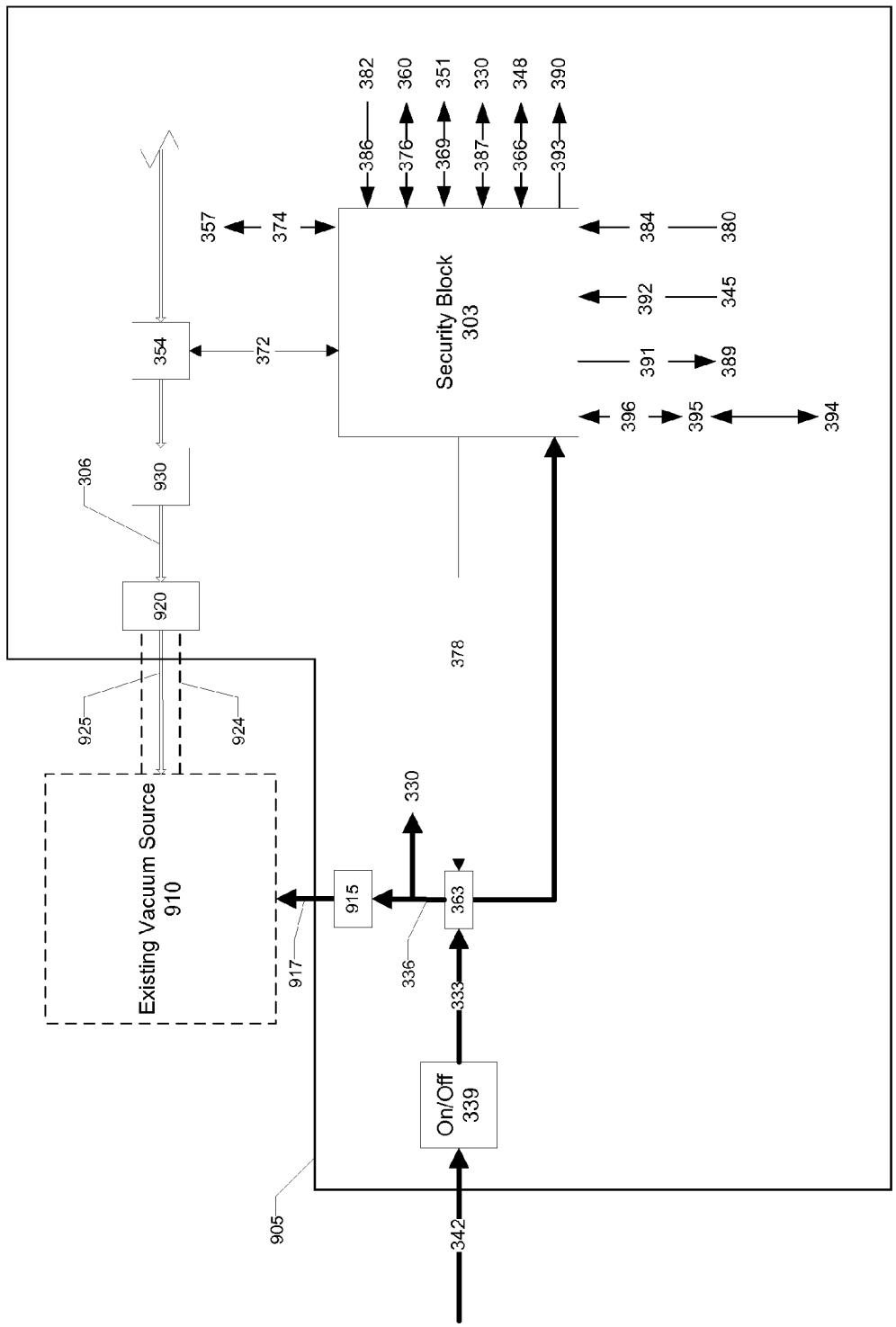
FIG. 9 shows a partial block diagram of the upgrade kit with the security mechanism according to the present invention.

FIG. 9 shows a partial block diagram of a microdermabrasion system upgrade kit 905. In the specific implementation shown in FIG. 9, the upgrade kit includes an electrical connector 915 connected to switch 363, a coupler 920 connected to vacuum pathway 306, and a vacuum adjustment control 930 on the vacuum pathway between the coupler and the wand (see FIG. 3). For sake of clarity, several other components that may also be included with the kit have been omitted from this diagram. These omitted components include the fluid reservoir, fluid pump, wand, tip, collection reservoir, and filter that are discussed above and shown in FIGS. 2 and 3.

An existing vacuum source 910 is shown connected to the upgrade kit. The existing vacuum source may include a vacuum line 924 in which there is a vacuum pathway 925. Vacuum pathway 925 is connected to vacuum pathway 306 via coupler 920.

Power is supplied to the existing vacuum source from electrical connector 915. That is, power is supplied through power input line 342 to on-off switch 339. From on-off switch 339 and switch 363, power is supplied via line 336 to electrical connector 915. From electrical connector 915, power is supplied via a line 917 to the existing vacuum source. Thus, in a specific embodiment, electrical connector 915 outputs power rather than inputs power. The output of power may be controlled by on/off switch 339, switch 363, the security block, or combinations of these. For example, in an implementation not including the security block, the output of power from electrical connector 915 is controlled by on/off switch 339.

In a specific embodiment, electrical connector 915 is a power socket (i.e., power receptacle or power outlet) so that it can accept an electrical plug from the existing vacuum source. Some examples of power sockets include type A and type B sockets. Type A and B sockets are typically found in the U.S. The type A socket has two slots to accept a plug having two flat parallel pins or blades. The type B socket has two slots and a hole to accept a plug having two flat parallel pins and a ground pin.

However, different parts of the world may use different types of sockets. For example, a type C socket is common in Europe. The type C socket accepts a plug having two 4 millimeter round pins that are spaced 19 millimeters apart. The U.S. Department of Commerce, International Trade Administration publication *Electric Current Abroad*, 1998 edition, reprinted 2002, which is incorporated by reference, describes different types of sockets used in different parts of the world, which are suitable for use as electrical connector 915 of the present invention.

In another embodiment, electrical connector 915 may be a terminal block (e.g., screw terminal and luster terminal) at which the electrical wires of the existing vacuum source are connected to the electrical wires of the upgrade kit.

In yet another embodiment, electrical connector 915 may be a plug and socket connector (e.g., male plug and female socket, hermaphroditic connector, crimp-on connector, and wire tap-in squeeze connector).

Coupler 920 connects vacuum pathway 925 to vacuum pathway 306. The coupler may be, for example, a double end barb coupler, a male hose tail, a female hose tail, a multistage hose tail, a push-to-connect coupler, a push-pull coupler, a reducing coupler (e.g., double end barb reducing coupler, compression fitting reducing coupler, and barbed reducing elbow) and the like.

The coupler may be a straight coupler or an angled coupler (e.g., 45 degree, 90 degree, and 135 degree). Angled couplers may be used where, for example, one or more turns are required to connect vacuum pathways 925 and 306.

Furthermore, although FIG. 9 shows only one coupler, it should be appreciated that other embodiments may include more than one coupler such as two, three, four, five, or more than five couplers. Use of multiple couplers allow, for example, two or more turns to be taken when connecting vacuum pathways 925 and 306.

The coupler may be made of plastic, nylon, or other crystallized polymers such as polypropylene or polyethylene. The coupler may be made of high density polyethylene (HDPE), glass filled nylon (GFN), polyvinylidene fluoride (PVDF), and the like. In alternative embodiments, the coupler may be made of metal such as brass, stainless steel, aluminum, titanium, and the like. The coupler may also be made of other materials such as carbon fiber, composites, or ceramics.

In a specific embodiment, coupler 920 is omitted. In this specific embodiment, a vacuum line of the upgrade kit may be coupled directly to a port on the existing vacuum source. In another embodiment, the vacuum line of the upgrade kit may be joined to vacuum line 924 of the existing vacuum source with an adhesive. Some examples of adhesives include natural adhesives (i.e., bioadhesives), synthetic adhesives such as elastomeric, thermoplastic, and thermosetting adhesives, drying adhesives (e.g., rubber cements), contact adhesives, hot adhesives (i.e., hot melt adhesives), reactive adhesives (e.g., epoxy), or pressure sensitive adhesives (e.g., tape, foil tape, duct tape, masking tape, electrical tape, polyester tape, polyethylene tape, polytetraflorethylene tape, and cloth tape).

The vacuum adjustment control may include a valve or a closeable-opening so that the flow rate through the vacuum line caused by the existing vacuum source can be adjusted. The valve may be, for example, a needle valve, ball valve, butterfly valve, control valve, gate valve, a globe valve, or a slide sleeve valve. It should be appreciated that in various embodiments, one or more vacuum adjustment controls may be provided in series with one another.

When the valve or closeable-opening is opened the existing vacuum source will draw air through the closeable-opening. This has the effect of lessening the amount of air or suction through the tip of the microdermabrasion hand piece. The amount of suction can be controlled by varying the size of the closeable-opening. For example, when the closeable-opening is fully opened the amount of suction at the tip will be less than when the closeable-opening is fully closed.

Adjustment of the valve or closeable-opening is through manual or electronic means. For example, where adjustment of the valve is through manual means a knob of the valve may be exposed on the console of the microdermabrasion system. The knob can then be turned by a user in order to open and close the valve and thus adjust the amount of suction at the hand piece. The knob may include any number of intermediate positions between fully closed and fully open. This allows the user to fine-tune the amount of suction at the hand piece.

As another example, where adjustment of the valve is through electronic means, the valve is coupled to the security circuit. The security circuit then sends a signal (e.g., analog or digital) to the valve that opens or closes the valve. The user can use a key pad on the microdermabrasion console in order to control the opening and closing of the valve. The valve may similarly include any number of intermediate positions between fully closed and fully open to allow fine tuning of the amount of suction at the hand piece.

In a specific embodiment, the vacuum adjustment control is located on the hand piece or near the hand piece. For example, the vacuum adjustment control may be located on vacuum line 202 (see FIG. 2) and positioned on the vacuum line such that a first distance from the vacuum adjustment control to the hand piece is less than a second distance from the vacuum adjustment control to the console. The first distance may range from about 1 centimeter to about 50 centimeters. Positioning the vacuum adjustment control on or near the hand piece allows the user to quickly adjust the suction force without having to reach over to the console.

Figure 10:
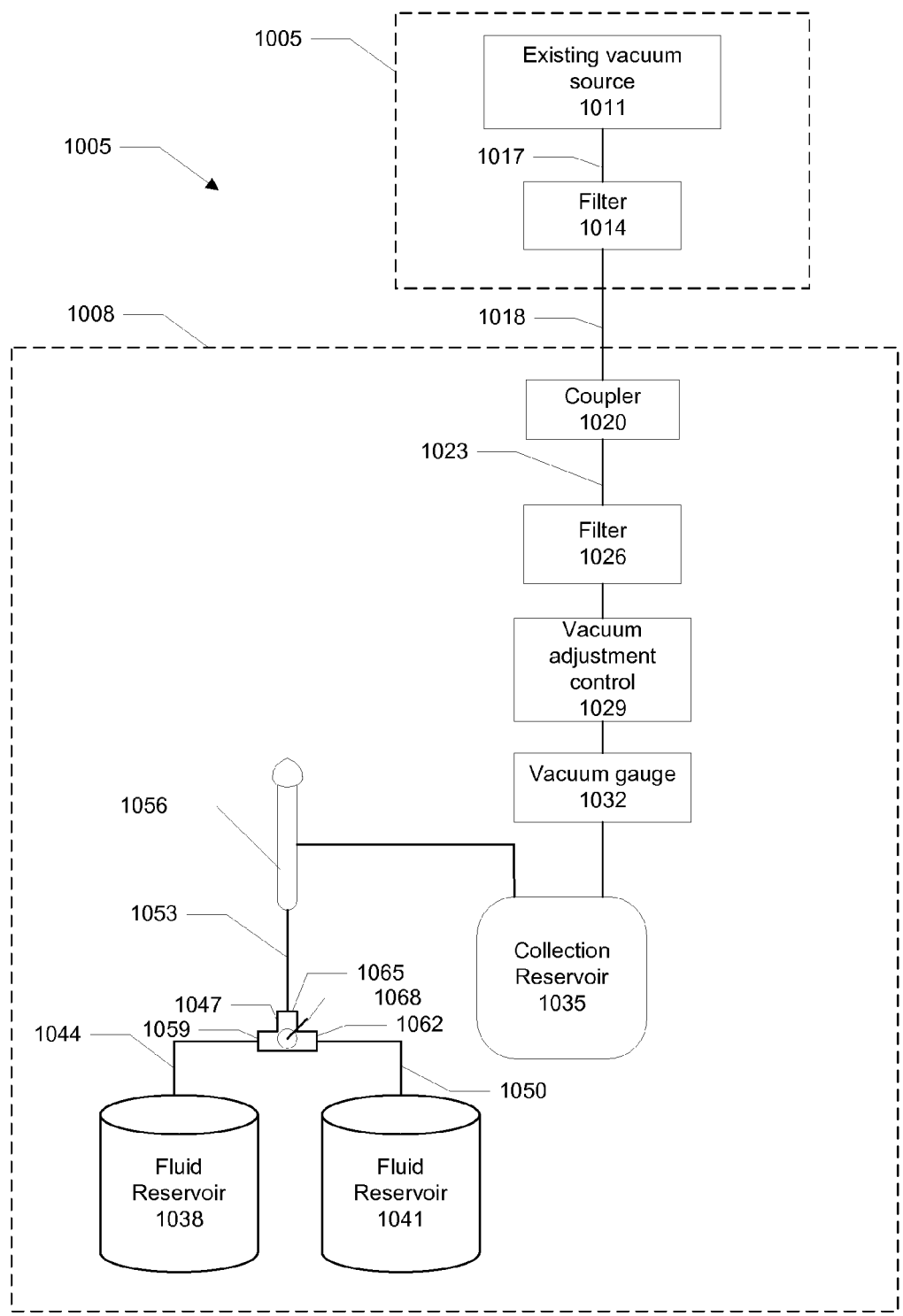
FIG. 10 shows a plumbing diagram of a specific implementation of an existing microdermabrasion system connected to the microdermabrasion upgrade kit.

FIG. 10 shows a plumbing diagram of a specific implementation of an existing microdermabrasion system 1005 connected to a microdermabrasion upgrade kit 1008 of the present invention.

In this implementation, the existing microdermabrasion system includes an existing vacuum source 1011 connected to a filter 1014 (e.g., hydrophobic filter) via a vacuum line 1017. However, in other implementations, the existing microdermabrasion system may not include filter 1014.

The microdermabrasion upgrade kit includes a coupler 1020 that connects a vacuum line 1018 with a vacuum line 1023 of the upgrade kit. The upgrade kit may also include a filter 1026 (e.g., overflow protection filter), which is connected to a vacuum adjustment control 1029, which is connected to a vacuum gauge 1032, which is connected to a collection reservoir 1035.

The upgrade kit may further include one or more fluid reservoirs or bottles, such as fluid reservoirs 1038 and 1041. A fluid line 1044 connects fluid reservoir 1038 to a joint 1047. A fluid line 1050 connects fluid reservoir 1041 to the joint. From the joint, a fluid line 1053 connects to a wand 1056, which connects to the collection reservoir.

In a specific implementation, the vacuum and fluid lines include tubing. The tubing may be flexible and may be made of plastic such as polyvinyl chloride (PVC), chlorinated polyvinyl chloride (CPVC), high density polyethylene (HDPE), cross linked polyethylene (PEX), low density polyethylene (LDPE), or nylon. The tubing may also be made of rubber, latex, neoprene (i.e., polychloroprene), or Kevlar®, just to name a few examples. In other implementations, the tubing may be include more rigid materials such as copper, stainless steel, steel, aluminum, cast iron, and the like. The tubing may also include a combination of different materials such as an aluminum layer placed between two layers of PEX. One benefit of this combination is that the PEX layers can provide chemical resistance while the aluminum layer allows the tubing to be shaped into various configurations.

The system may also include one or more valves placed at various locations in the vacuum lines, fluid lines, or both to permit or block the vacuum and fluid paths as discussed above and shown in FIG. 3.

Joint 1047 may be a valve. In the example shown in FIG. 10, the joint is a three way valve with two input ports 1059 and 1062, one output port 1065, and a handle 1068.

The handle may further include multiple location settings so that by turning the handle to a certain position, the valve can completely shut off the flow of fluid from fluid reservoir 1038 and permit the flow of fluid from fluid reservoir 1041, completely shut off the flow of fluid from fluid reservoir 1041 and permit the flow of fluid from fluid reservoir 1038, completely shut off the flow of fluid from both fluid reservoirs, or permit fluid to flow from both fluid reservoirs such that the output of fluid from output port 1065 is a mixture of fluids.

Thus, fluid reservoirs 1038 and 1041 may each contain different types of fluid (e.g., topical and disinfectant). The valve may be used to permit only a certain type of fluid to flow to the wand or to allow a mixture of fluid to flow to the wand. By varying the position of the handle, the user can mix the fluids in any proportion.

In a specific implementation, the position of the handle is manually controlled by the user. In other implementations, the position of the handle may be electronically controlled by the system.

Some examples of valves that are suitable for use in an embodiment of the invention include diverter valves, butterfly valves, ball valves, needle valves, pinch valves, and solenoid valves. In another implementation, joint 1047 may be a manifold. The joint may have any number of inlet and outlet ports that can each be completely open, completely closed, partially open, or partially closed to permit mixing or blending of fluids.

Figure 11:
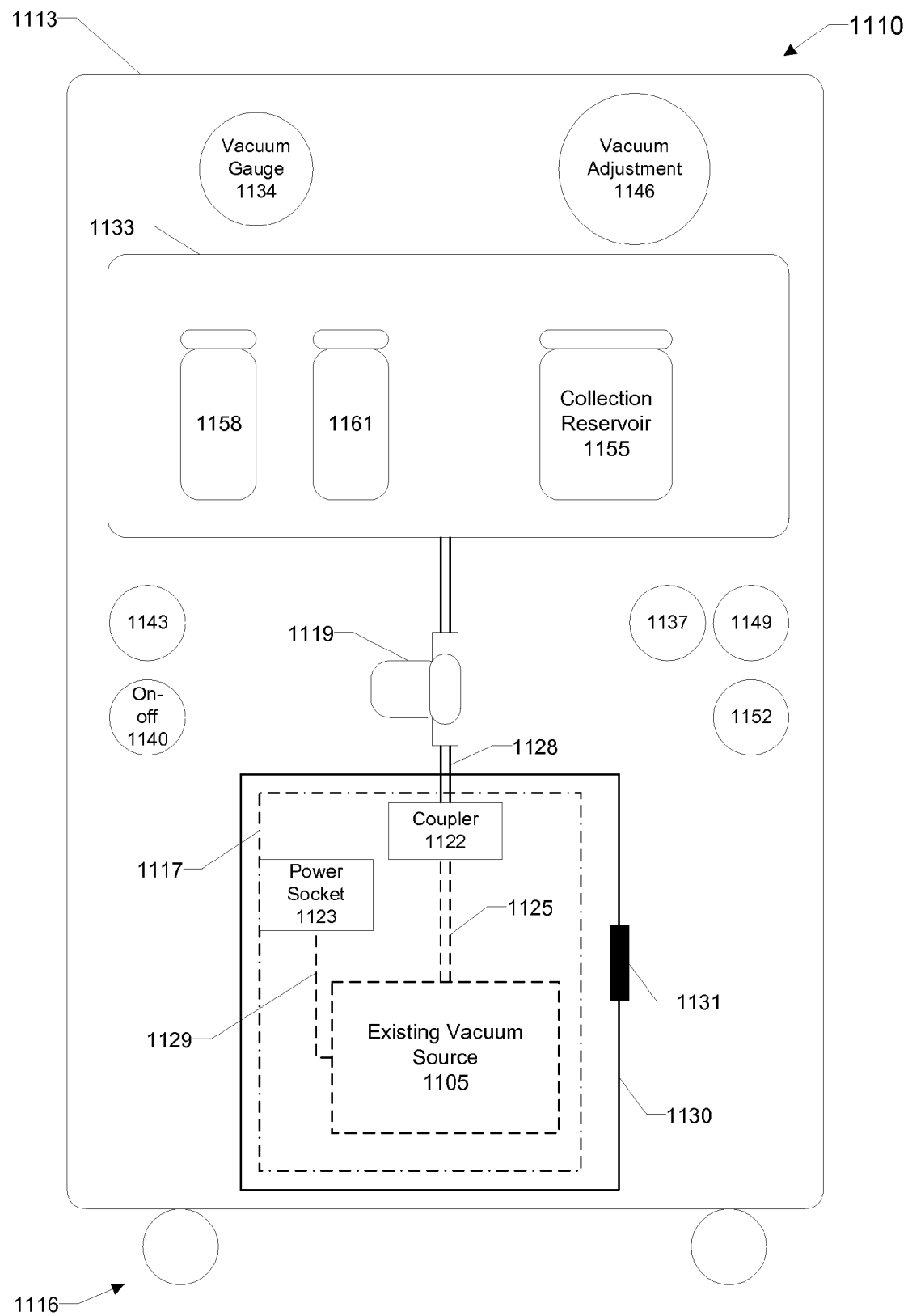
FIG. 11 shows a specific implementation of an existing vacuum source connected to the upgrade kit.

FIG. 11 shows a specific implementation of an existing vacuum source 1105 connected to a microdermabrasion upgrade kit 1110. In this implementation, the upgrade kit and an existing vacuum source 1105 are housed in a cart or cabinet 1113 which is moveable via wheels 1116 that are connected to the cabinet. Inside the cabinet in a cavity 1117 are the various internal components of the microdermabrasion system. In a specific embodiment, the cavity includes a coupler 1122 and a power socket 1123. In other embodiments, the cavity also includes a filter 1119.

Coupler 1122 is between the filter and the existing vacuum source. The coupler connects a vacuum line 1125 of the existing vacuum source to a vacuum line 1128 of the upgrade kit.

The cabinet helps to hide or obscure from view the various internal components so that the system appears attractive and aesthetically pleasing. The cabinet may include a barrier 1130 with a handle 1131. In a specific embodiment, the barrier is a door that is hinged along one side so that the door can be opened and closed. The door includes a locking mechanism so that the door does not accidentally open. The locking mechanism may be a magnet catch, a friction catch, a grabber catch, barrel catch, roller catch, a bolt latch, a lock and key, and the like.

In various other embodiments, the door may slide along tracks, pivot on one or more hinges, fold, or slide between two other panels (e.g., pocket door). Some examples of doors include left-hand reverse doors, right-hand reverse doors, left-hand doors, right-hand doors, and double doors. In other embodiments, the barrier is a removable panel. The removable panel may be fastened to the console with screws (e.g., slotted screws, Phillips head screws, and thumb screws). In another embodiment, the barrier is a drape or curtain, such as a cloth drape.

The cavity may have any shape, but typically has the shape of a box such as a rectangular box or square box. Generally, the cavity is defined by a first sidewall, a second sidewall opposite the first sidewall, a base, a top opposite the base, and a back wall opposite the barrier.

In a specific embodiment, the cavity has the shape of a rectangular box. For example, the first sidewall lies on a first plane, the second sidewall lies on a second plane, the base lies on a third plane, the top lies on a fourth plane, the back wall lies on a fifth plane, and the door lies on a sixth plane. The first plane is parallel to the second plane. The third plane is parallel to the fourth plane. The fifth plane is parallel to the sixth plane. All the planes intersect at perpendicular angles.

The lengths and widths of the first and second sidewalls are the same. And the lengths and widths of the base and top are the same. The length of the first and second sidewalls are greater than the widths of the base and top. That is, the short sides of the rectangular box form the base and top and the long sides of the rectangular box form the first and second sidewalls.

In other embodiments, the cavity has a different shape (e.g., cylinder and dome). Since existing microdermabrasion systems and vacuum sources are manufactured in a variety of shapes, this range of shapes for the cavity helps to ensure that most, if not all, existing microdermabrasion systems or vacuum sources will be able to fit into the cavity.

The cavity is typically an empty space so that it will be able to accommodate the existing vacuum source. For example, one or more space diagonals can pass from one corner of the box or cavity, through the center of the box, and to the opposite corner without intersecting any component. The existing vacuum source is shown as a dotted line since the existing vacuum source is not included in an implementation of the invention. However, the cavity may include the power socket, coupler, or both.

The volume of the cavity ranges from about 7000 cubic centimeters to about 60000 cubic centimeters. Since existing vacuum sources are manufactured in a variety of sizes, this range helps to ensure that most, if not all, existing vacuum sources will be able to fit into the cavity. Furthermore, in some cases users may not want to remove the existing vacuum source from their existing microdermabrasion system. Thus, the cavity is designed to accommodate the user's existing microdermabrasion system including the existing vacuum source.

In a specific implementation, the microdermabrasion upgrade kit is available in multiple versions with each version including a cavity having a different volume, different shape, or both. For example, a first embodiment includes a small sized cavity shaped as a rectangular box that has a volume that ranges from about 7000 cubic centimeters to about 20000 cubic centimeters. A second embodiment includes a medium sized cavity shaped as a square box that has a volume that ranges from about 20000 cubic centimeters to about 40000 cubic centimeters. A third embodiment includes a large sized cavity shaped as a cylinder that ranges from about 40000 cubic centimeters to about 60000 cubic centimeters.

Generally, it will be desirable to select a microdermabrasion upgrade kit with the smallest sized cavity which will fit the user's existing microdermabrasion system or vacuum source. The upgraded microdermabrasion system will then take up a minimum amount of space in the treatment room.

The cavity may further include fasteners such as straps, brackets, or both so that the user can secure the existing vacuum source to the cavity. For example, these fasteners may be attached to a sidewall of the cavity. This will help to prevent the existing vacuum source from shifting inside the cabinet. Some examples of straps include hook-and-loop straps and buckle straps. Some examples of brackets include angle brackets and flat brackets.

The power socket, which supplies output power to the existing vacuum source is typically mounted on the first or second sidewall. For example, the power socket may be mounted into a recess or opening in the sidewall so that it is flush with the surface of the sidewall. The existing vacuum source can rest on the base while an electrical cord 1129 of the existing vacuum source is plugged into the power socket. However, in other embodiments, the power socket may be mounted in a different location such as on the base, top, or back wall.

Since the microdermabrasion upgrade kit is typically packaged without a vacuum source, the power socket will be empty or otherwise not have a plug plugged into it.

In a specific embodiment, vacuum line 1128 extends through an opening and into the cavity. For example, vacuum line 1128 extends through an opening in the top of the cavity, or through an opening in the first or second sidewalls of the cavity. In another embodiment, vacuum line 1128 terminates at an opening in the cavity and a coupler is inserted into the opening. For example, the coupler is a male hose tail coupler with a threaded end screwed into the opening and a barbed end that is exposed in the cavity.

Thus, in various embodiments, the coupler will have at least one end, i.e., the end intended to be connected to vacuum line 1125 uncoupled. The opposite end of the coupler which will be connected to vacuum line 1128 of the upgrade kit may also be unconnected since the particular size of the user's existing vacuum line 1125 will generally not be known.

However, in other embodiments, the coupler will be connected to vacuum line 1128. For example, the manufacturer of the upgrade kit may select what it believes to be the most popular coupler size (e.g., 6.4 millimeters (¼ inch) and 7.9 millimeters (5/16 inches)). If the coupler is the wrong size for the user's existing vacuum source then the user will remove the coupler, select a coupler having the proper size from the coupler kit, and insert the new coupler into vacuum line 1128.

The cabinet further includes a bottle holder assembly 1133, various displays such as a vacuum gauge 1134, an overflow indicator 1137, various controls such as an on-off switch 1140, a fluid selection switch 1143, and a vacuum adjustment control 1146. The cabinet may also include a vacuum port 1149 and a fluid port 1152.

The bottle holder assembly includes a collection reservoir 1155 and one or more bottles of fluid such as a topical fluid 1158 and a disinfectant fluid 1161.

The fluid selection switch allows the user to switch between two or more bottles of fluid. For example, a microdermabrasion treatment may start with the disinfectant fluid applied to the patient's skin which is then followed by a topical fluid applied to the skin. With the fluid selection switch, the user can switch from the disinfectant fluid to the topical fluid without having to first remove the previous bottle (i.e., the disinfectant) and replace it with the next bottle (i.e., the topical). This feature can save the user valuable time because they do not have to constantly remove and replace bottles.

The vacuum and fluid ports allow the wand to be permanently or removeably connected to the system. For example, in a specific implementation, the wand is connected to the ports using tubing. The ports may have a locking feature to help prevent the wand from being accidentally disconnected. For example, the ports may include twist lock couplers (e.g., twist to lock and untwist to unlock) to secure the tubing to the ports.

The on-off switch supplies power to the system. The overflow indicator alerts the user if the collection reservoir is full. When the collection reservoir is full, the security circuit of the system discussed above and shown in FIG. 3, helps to prevent the collection reservoir from overflowing. For example, the security circuit may close one or more valves, shut off power to one or more components, or combinations of these.

The vacuum adjustment control allows the user to vary the suction or vacuum pressure. The amount of suction (e.g., 2, 4, 6, 8, or 10 pounds per square inch) may be displayed on the vacuum gauge.

One or more filters, such as filter 1119, help to prevent fluid from entering the vacuum source. The filter may be a hydrophobic filter, an overflow protection filter, and the like.

In other embodiments, the microdermabrasion upgrade kit does not include the cavity for the existing vacuum source. The absence of the cavity allows the upgrade kit to be packaged into a smaller and lighter enclosure which takes up less space. That is, the enclosure has dimensions which are insufficient for housing a vacuum pump. This is desirable because shipping, packaging, and material costs for the upgrade kit will be less expensive. Manufacturing costs will also be less expensive. For example, the enclosure will not include a forced air output vent that may be needed for the vacuum source to operate. The vacuum source is external to the upgrade kit. The upgrade kit may include instructions (e.g., instruction manual, video disc, and tutorial) which show the user how to connect an external vacuum source to the upgrade kit.

In a specific embodiment, the upgrade kit does not include the cavity, but includes the power socket and vacuum adjustment control including a vacuum pump pressure display. This allows the existing vacuum source to be plugged into (or electrically connected) to the upgrade kit which will then supply electrical power to the existing vacuum source. The vacuum adjustment control allows the user to vary the amount of suction at the hand piece. Turning on the power to the upgrade kit (i.e., turning on the first switch) turns on the vacuum pump pressure display of the console. In an embodiment not including the security circuit, power will also be sent to the power socket. In another embodiment including the security circuit, power will not be sent to the power socket until the security circuit sends a signal to a switch which connects the power supply to the power socket.

In another embodiment, the upgrade kit does not include the cavity and does not include the power socket. Instead, the existing vacuum source receives electrical power from a different power source and only the vacuum lines of the upgrade kit and existing vacuum source are connected.

Figure 12:
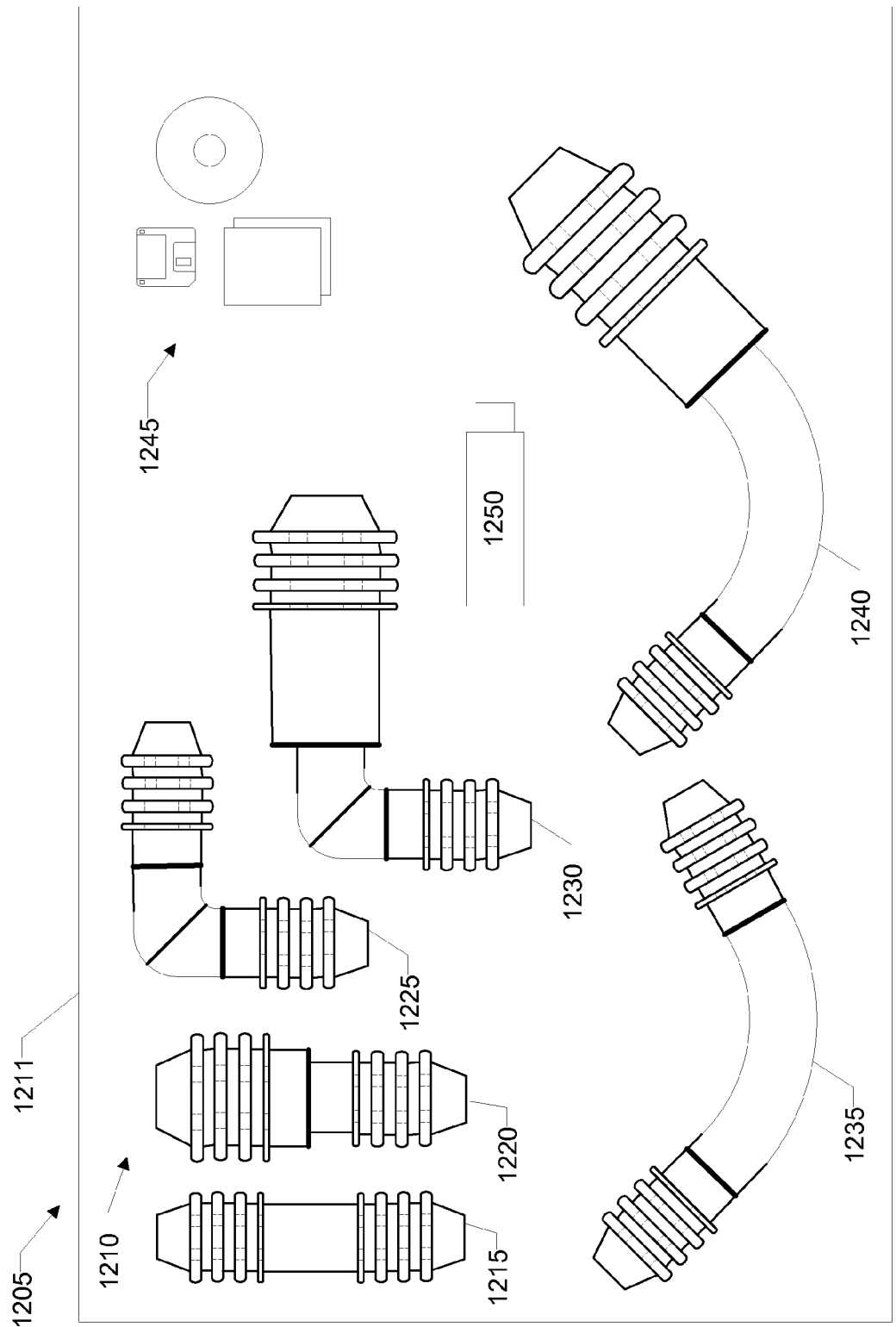
FIG. 12 shows a first implementation of a coupler kit.

FIG. 12 shows a first implementation of a packaging option for the couplers. In a specific implementation, the couplers are provided as a coupler kit 1205. The kit includes couplers having the same sizes (e.g., same outer diameters), couplers having different sizes (e.g., different outer diameters), couplers having different angles or bends (e.g., 45 degree, 90 degree, and 135 degree), different types of couplers (e.g., double end barb couplers, male hose tail couplers, and female hose tail couplers), or combinations of these. The kit also includes instructions 1245 and an adhesive 1250.

In this specific implementation, the coupler kit includes an assortment of double end barb couplers 1210 having varying outer diameters and bends. The couplers are placed into a container 1211. The container includes a base member, a recloseable lid, and a tray that fits in the base member. The recloseable lid may be made of a transparent material such as clear plastic so that the items in the kit are visible. In an embodiment, the recloseable lid and base member connected with a hinge that allows the recloseable lid to swing open and swing close (e.g., clamshell container).

The tray includes cavities to hold the couplers. In various embodiments, the tray is made of plastic, foam, or polypropylene. The tray may include an area for a company logo and labels adjacent to the cavities which identify the coupler. Some examples of labels include stickers and tags. In other embodiments, the labels are molded with or imprinted onto the tray. The labels may include text (e.g., ¼ inch straight coupler, $5/16$ inch angle coupler, and ⅜ inch to ¼ inch reducing coupler). In other embodiments, the labels are color, number, or letter codes which identify the type of coupler. In this embodiment, a color, number, or letter legend is provided so that users can identify the coupler type using the color, number, or letter codes.

The coupler kit includes six couplers including couplers 1215, 1220, 1225, 1230, 1235, and 1240. However, it should be appreciated that in other implementations there may be less than six couplers (e.g., two, three, four, or five couplers) or more than six couplers (e.g., seven, eight, nine, ten, or more than ten couplers).

Coupler 1215 is a straight coupler having ends with the same diameters. Coupler 1220 is a straight coupler having ends with different diameters (i.e., reducing coupler). Coupler 1225 is a right angle or 90-degree coupler having ends with the same diameters. Coupler 1230 is a right angle coupler having ends with different diameters. Couplers 1235 and 1240 are both 135-degree couplers. Coupler 1235 has ends with the same diameter. Coupler 1240 has ends with different diameters.

The coupler kit allows the user to select a coupler having an end that will slip into the vacuum line of the user's existing vacuum source. For example, existing vacuum sources may each have vacuum lines of varying inner diameters because these vacuum sources may be from different manufacturers. Thus, with the coupler kit, the user can select that coupler which offers the best fit.

Generally, the coupler with the best fit will be that coupler that has an outer diameter similar to the inner diameter of the vacuum line of the existing vacuum source. In a specific implementation, the outer diameter of the coupler will be slightly larger than the inner diameter of the vacuum line into which the coupler is to be inserted. This helps ensure a snug or airtight fit between the vacuum line of the existing vacuum source and the vacuum line of the upgrade system.

In a specific embodiment, an end of all the couplers will have the same outer diameter. This is because that end of the coupler is the end that will be inserted into the vacuum line of the upgrade kit and the diameter of that vacuum line will be known. That end may include a marking. The marking may include text, paint, tape, a protrusion, an indentation, or other visual or tactile distinction to indicate that it is the end to be inserted into the vacuum line of the upgrade system.

It should be appreciated that in other embodiments, the marking may be reversed. That is, the end of the coupler that includes the marking indicates the end of the coupler that is to be inserted into the existing vacuum line while the end of the coupler that is not marked is to be inserted into the vacuum line of the upgrade system.

The outer diameters of the couplers may range from about 1.6 millimeters ($1/16$ inch) to about 25.4 millimeters (1 inch). This includes, for example, 2.4 millimeters ($3/32$ inches), 3.2 millimeters (⅛ inch), 4.0 millimeters ($5/32$ inches), 4.8 millimeters ($3/16$ inches), 6.4 millimeters (¼ inch), 7.9 millimeters ($5/16$ inches), 9.5 millimeters (⅜ inches), 12.7 millimeters (½ inch), 15.9 millimeters (⅝ inches), 19.0 millimeters (¾ inches), and 25.4 millimeters (1 inch). In some embodiments, the outer diameter of a coupler is less than 1.6 millimeters ($1/16$ inch) or more than 25.4 millimeters (1 inch). This variation in sizes helps to ensure that the user will be able to find a coupler in the coupler kit that will fit into the vacuum line of the user's existing vacuum line.

Each of the couplers may be marked to indicate their size (e.g., diameters). For example, the couplers may be color coded. That is, red indicates ⅛ inch coupler, blue indicates $5/32$ inch coupler, yellow indicates $3/16$ inch coupler, green indicates $5/16$ inch coupler, pink indicates ⅜ inch coupler, and so forth. A color legend is included with the coupler kit so that the user can match the color on the coupler with the size of the coupler. In other embodiments, a sticker or a tag with the coupler size is attached to the coupler.

In a specific implementation, the coupler kit is packaged with the microdermabrasion upgrade kit. In other implementations, the coupler kit is packaged separately from the upgrade kit. This allows the user to purchase the upgrade kit and then select the coupler kit having those couplers which will fit the vacuum line and vacuum line routing of the user's existing microdermabrasion vacuum source. For example, a first embodiment of the coupler kit may include straight couplers having ends with different diameters. A second embodiment of the coupler kit may include angled couplers having ends with the same diameters. A third embodiment of the coupler kit may include both straight and angled couplers having ends with different diameters, and so forth.

Instructions 1245 may be provided on any medium, such as paper, DVD, CD, video cassette, tape cassette, and the like. For example, the instructions may be provided as a portable document format (PDF) file on a CD or printed in a pamphlet. The instructions direct the user on how to upgrade their existing microdermabrasion system. The instructions include information on how to remove the existing vacuum source and connect it to the microdermabrasion upgrade system. In a specific embodiment, the instructions include a ruler with measuring units (e.g., inches, millimeters, and centimeters). The ruler may be printed on a page of the pamphlet or be separate from the pamphlet. The user can remove or tear out the page of the pamphlet which includes the ruler and use the ruler to measure the size (e.g., diameter) of the vacuum line of their existing microdermabrasion vacuum source. With this size, the user can then select that coupler with a similar size and use that coupler to connect their existing vacuum source to the microdermabrasion upgrade system.

An implementation of the coupler kit includes adhesive 1250. The adhesive can be applied by users to the coupler ends when the user connects the vacuum line from their existing vacuum source to the vacuum line of the upgrade kit. Some examples of adhesives include epoxy, glues, or rubber cement.

Figure 13:
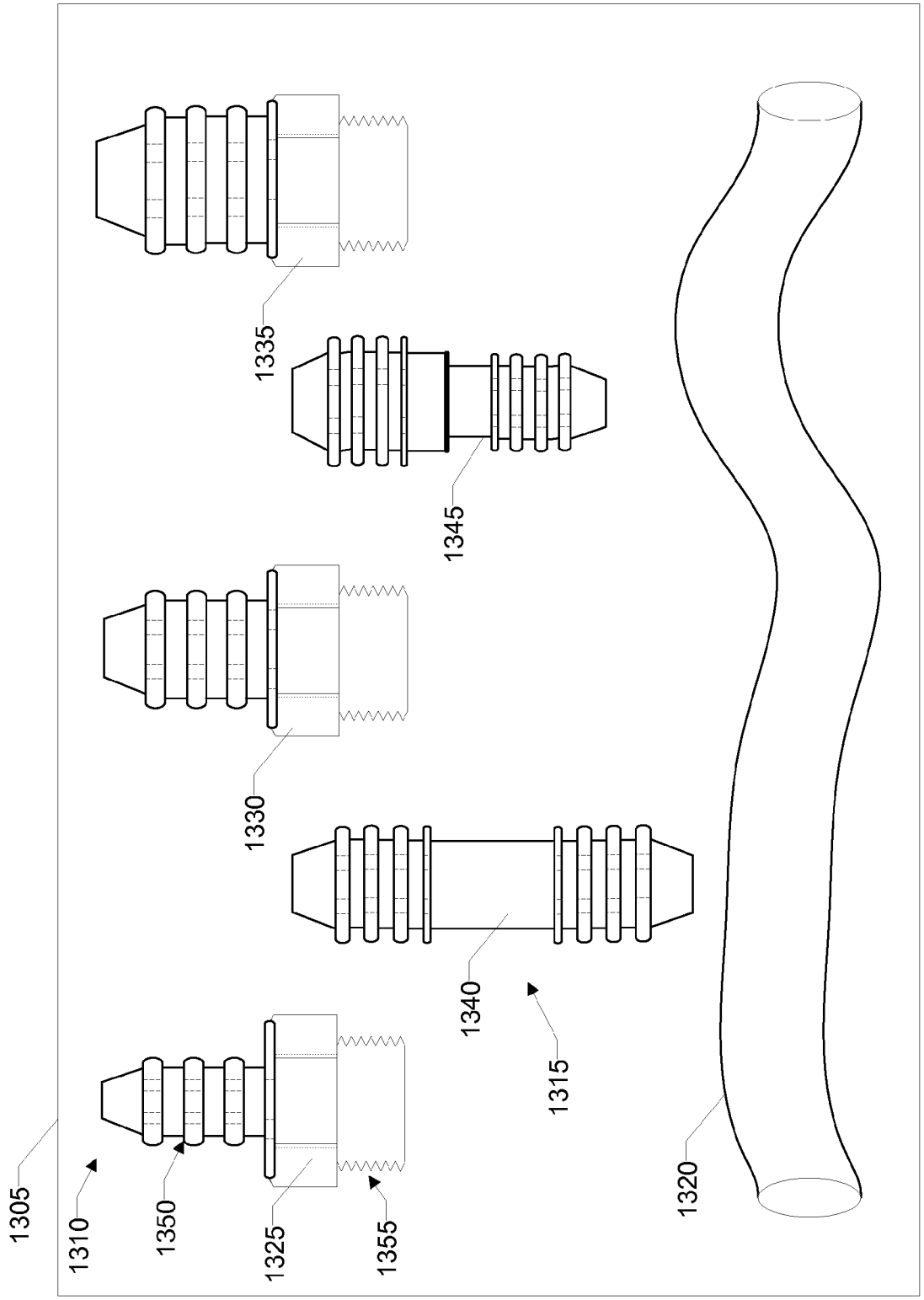
FIG. 13 shows a second implementation of a coupler kit.

FIG. 13 shows a second implementation of a packaging option for the couplers. In this implementation, a coupler kit 1305 includes an assortment of male hose tail couplers 1310, an assortment of double end barb couplers 1315, and tubing 1320. In this implementation, there are three male hose tail couplers (1325, 1330, and 1335) and two double end barb couplers (1340, and 1345) for a total of five couplers. It should be appreciated, however, that a coupler kit may contain any number and any type of coupler in any combination.

In the example shown in FIG. 13, each of the male hose tail couplers have barbed ends 1350 and threaded ends 1355. Each barbed end has an outer diameter that is different from the outer diameter of the other barbed ends. Each threaded end has an outer diameter that is the same as the other threaded ends.

In a specific implementation, the user selects a male hose tail coupler that has an outer diameter at the barbed end that is similar to the inner diameter of the vacuum line of the existing vacuum source. The user then screws the threaded end of the coupler into a socket that connects to the vacuum line of the system. The user then connects the vacuum line of the existing vacuum source to barbed end of the coupler.

In the example shown in FIG. 13, double end barb coupler 1340 has first and second barbed ends having the same outer diameter. Double end barb coupler 1345 has first and second barbed ends having different outer diameters.

In a specific implementation, the double end barb couplers and the tubing may be used to form an extension between the existing vacuum source and the system. For example, the vacuum line of the existing vacuum source may not be long enough to reach the socket that connects to the vacuum line of the system. Coupler 1340 can then be used to connect an end of the vacuum line of the existing vacuum source to tubing 1320 which in turn can be connected to the barbed end of the male hose tail coupler. Coupler 1345 can be used instead of coupler 1340 if, for example, the vacuum line of the existing vacuum source has a different inner diameter than the inner diameter of tubing 1320.

The length of tubing 1320 may vary. In a specific implementation, the length of the tubing ranges from about 0.6 meters to about 1.2 meters. For example, the tubing may be about 0.7, 0.8, 0.9, 1.0, 1.1, or 1.2 meters long or greater. In some implementations, the tubing may be less than 0.6 meters.

Although the figure shows one piece of tubing, it should be appreciated that in other embodiments there will be more than one piece of tubing (e.g., two, three, four, or more than four pieces of tubing).

The inner diameter of the tubing may range from about 1.6 millimeters (1/16 inch) to about 25.4 millimeters (1 inch). This includes, for example, 2.4 millimeters (3/32 inches), 3.2 millimeters (1/8 inch), 4.0 millimeters (5/32 inches), 4.8 millimeters (3/16 inches), 6.4 millimeters (1/4 inch), 7.9 millimeters (5/16 inches), 9.5 millimeters (3/8 inches), 12.7 millimeters (1/2 inch), 15.9 millimeters (5/8 inches), 19.0 millimeters (3/4 inches), and 25.4 millimeters (1 inch). In some embodiments, the inner diameter of the tube is less than 1.6 millimeters (1/16 inch) or more than 25.4 millimeters (1 inch).

The tubing may be made of a material that can be easily cut or trimmed by the user. The tubing may be flexible and may be made of plastic such as polyvinyl chloride (PVC), chlorinated polyvinyl chloride (CPVC), high density polyethylene (HDPE), cross linked polyethylene (PEX), low density polyethylene (LDPE), or nylon. The tubing may also be made of rubber, latex, neoprene (i.e., polychloroprene), or Kevlar®, just to name a few examples. In other implementations, the tubing may be include more rigid materials such as copper, stainless steel, steel, aluminum, cast iron, and the like. The tubing may also include a combination of different materials such as an aluminum layer placed between two layers of PEX.

Figure 14:
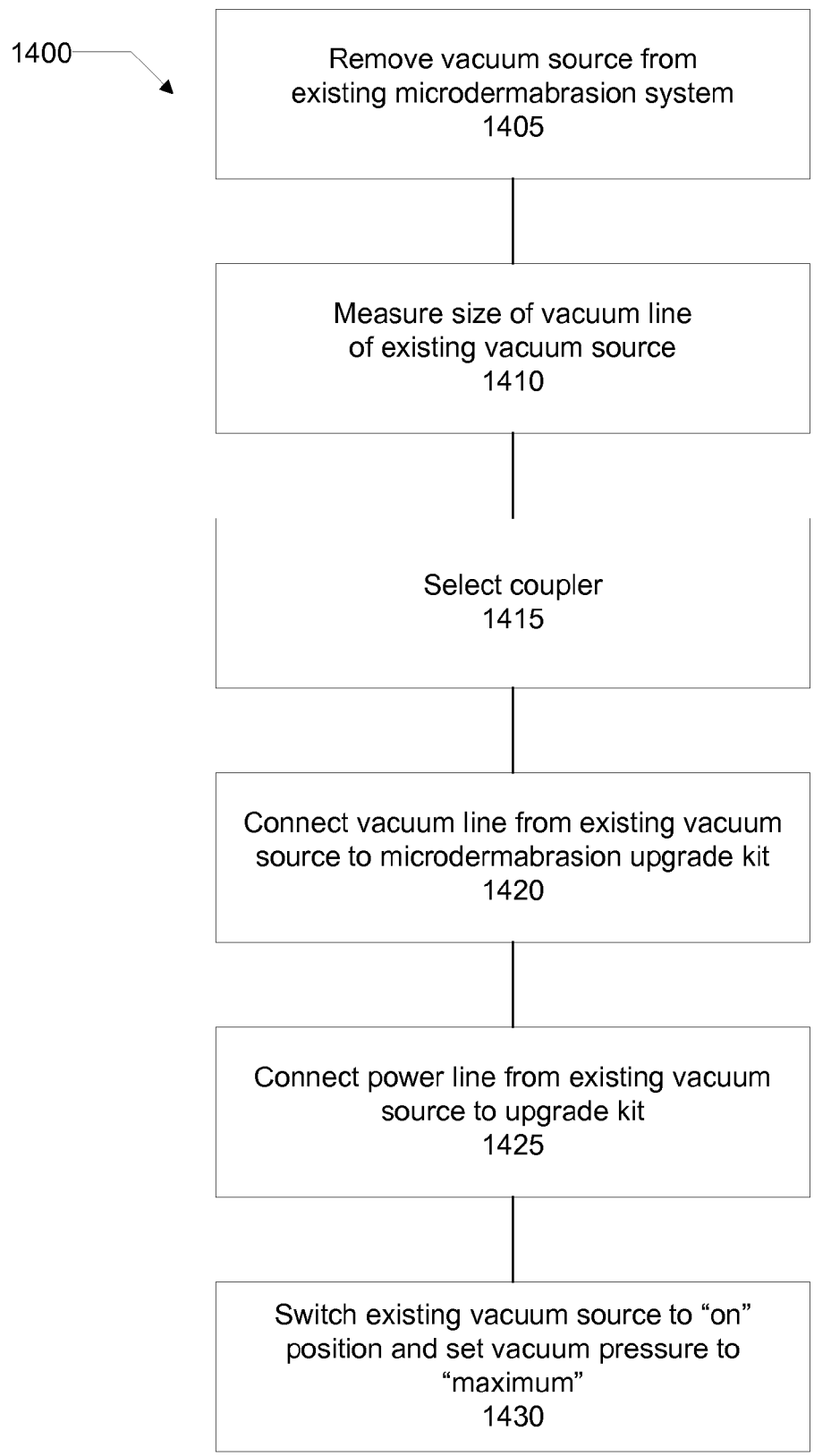
FIG. 14 shows a flow diagram for upgrading an existing microdermabrasion system.

FIG. 14 shows a flow diagram 1400 for upgrading an existing microdermabrasion system with the microdermabrasion upgrade kit in an implementation of the invention. In a step 1405, the user removes the existing vacuum source from their existing microdermabrasion system. The removal may include cutting the vacuum line between the existing microdermabrasion vacuum source and the existing microdermabrasion wand or hand piece. The removal may further include disconnecting the existing vacuum source from the power supply (e.g., unplugging existing vacuum source from outlet).

In a step 1410, the user measures the size of the vacuum line of the existing vacuum source. For example, where the existing vacuum line includes tubing, the measurement includes measuring the inner diameter of the existing vacuum line.

In a step 1415, the user selects a coupler. The selected coupler will generally have an outer diameter that is similar to the inner diameter of the existing vacuum line. In an implementation including a barb coupler having first and second barbed ends, the outer diameter of the first end of the coupler will typically be slightly larger than the inner diameter of the existing vacuum line. This allows, for example, a tight and secure connection between the coupler and the vacuum line.

In a step 1420, the user connects the vacuum line from the existing vacuum source to the system using the coupler. For example, after the user selects the coupler, the user inserts the first barbed end of the coupler into the vacuum line of the existing vacuum source. The user then inserts the second barbed end of the coupler into the vacuum line of the system.

In a specific implementation, the user may heat one or both ends of the vacuum lines before inserting the coupler into the vacuum lines. Some examples of heating sources that may be used to heat the vacuum lines include hair dryers, heat guns, hot water (e.g., submersing an end of the vacuum line in boiling water), torches, blowtorches, and lighters. Heating the vacuum lines may result in the vacuum lines expanding and becoming pliable which may ease the insertion of the coupler into the vacuum lines.

In yet another implementation, the user may cool the coupler before inserting the coupler into the vacuum lines. For example, the user may place the coupler in a freezer or refrigerator or submerge the coupler in ice. Cooling the coupler may contract or shrink the coupler which may ease the insertion of the coupler into the vacuum lines.

The first and second barbed ends of the coupler may be further secured to their respective vacuum lines by, for example, a hose clamp, a nylon tie, an adhesive (e.g., epoxy), or the like to prevent the barbed coupler from being pulled out of the vacuum lines.

In a step 1425, the user connects the power line from the existing vacuum source to the system. This includes electrically coupling the power line to the electrical connector shown in FIG. 9. For example, the connection may include plugging a power cord from the existing vacuum source into the electrical connector.

In a step 1430, the user switches the existing vacuum source to the "on" position and sets the vacuum pressure on the existing vacuum source to "maximum." This is because in a specific implementation, both the vacuum pressure and power supply to the existing vacuum source will be controlled by the security block of the microdermabrasion upgrade kit.

Figure 15:
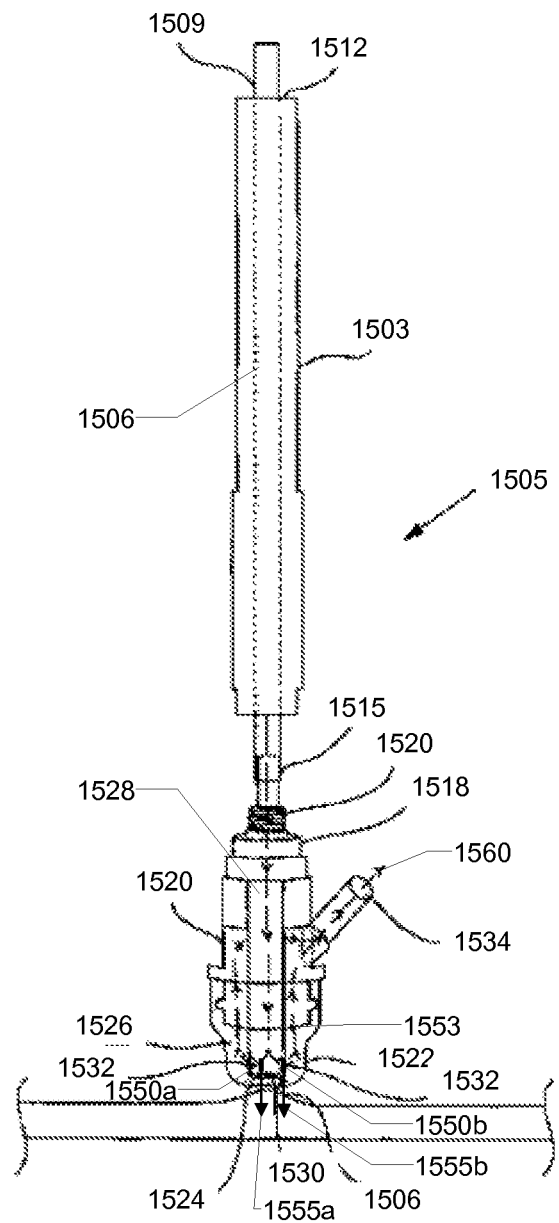
FIG. 15 shows an exploded view of an embodiment of a microdermabrasion hand piece.

FIG. 15 shows a partially exploded view of a specific implementation of a microdermabrasion hand piece 1505 that may be included with the microdermabrasion upgrade kit. The hand piece is designed to be handheld by a user for its application to a skin 1506 of a patient in the performance of microdermabrasion and radiation therapy. As such, it may be designed with an elongated handle 1503 to facilitate grasping by a user. One of ordinary skill in the art will appreciate that many different shapes and materials may be employed for the handle and the present invention is not to be limited to an elongated, substantially cylindrical handle as shown.

One or more radiation sources 1550*a*, 1550*b* may be located outside a periphery of an abrasive member or tip 1530 (e.g., abrasive region). The radiation sources may be positioned between an annulus 1526 and a passageway 1528. For example, the radiation sources may be located on a shoulder 1553 of a functional block 1518. In yet another embodiment, the radiation sources may be located on a treatment tip 1522. The radiation sources are positioned to emit radiation 1555*a* and 1555*b* into the patient's skin.

In the example of FIG. 15, the handle is made of plastic, such as nylon or other plastic having sufficient toughness and mechanical strength, but may also be made of metal, such as stainless steel, for example, or ceramics or composites. The handle is annular or tubular, providing a passageway 1506 through which tube 1509 is extended.

Tube 1509 is adapted to be connected at its proximal end 1512 (the end extending away from handle 1503) to a fluid reservoir (see FIG. 2) which is in turn, open to atmosphere. The tube is flexible and may be made of PVC or other compatible plastic, for example. Similarly, all other vacuum lines described herein are flexible to afford maneuverability to the hand piece and may be made of PVC or other compatible plastic. Alternatively, the proximal end of tube 1509 can be left open to atmosphere or connected to a flow control valve, filter, or both, with or without connection to fluid reservoir.

A distal end 1515 of tube 1509 is connected to functional block 1518, by a frictional fit, as shown. Alternatively, a clamp or other type of connector may be provided to facilitate a pressure tight seal between tube 1509 and the functional block. The functional block is adapted to be fixed to the handle and may be machined from metal such as surgical stainless steel or may be machined or molded of plastic or casted or molded from ceramic. The functional block may be fixed to the handle using threads 1520 or other mechanical or chemical equivalent, although the fixation or interconnection is preferably done so that the functional block can readily be detached and reconnected easily.

A vacuum head base 1520 is fitted over functional block 1518 to form a pressure tight seal therewith. The vacuum head base may be machined from metal such as surgical stainless steel or may be machined or molded of plastic or casted or molded from ceramic. The vacuum head base may be frictionally fit over the functional block with a seal being effectuated by positioning one or more O-rings or other sealing members between the functional block and vacuum head base 1520.

Treatment tip 1522 is fitted over the end of the vacuum head base, and, likewise may be friction fit, provided with threads, or both or other attachment means to provide a pressure tight fit between the components. The treatment tip is smooth surfaced and adapted to glide over the skin surface for application of lotions, vitamins or other fluids thereto during processing. The treatment tip may be made of plastic such as nylon or glass, such as Pyrex, for example and is preferably, although not necessarily transparent or translucent. A transparent treatment tip allows better visualization by the operator during processing.

One or more O-rings or other sealing members may be provided between vacuum head base 1520 and the treatment tip to facilitate the pressure tight seal. Alternatively, the treatment tip may be integrally machined or molded with the vacuum head base.

The treatment tip includes an opening 1524 which targets an area of skin to be microabraded when the treatment tip is applied to the skin. Although shown with a single large opening 1524, it is conceivable that the treatment tip could be provided with more than one opening to perform a similar function as described below.

Functional block 1518 is a tubular structure that is configured to mate with vacuum head base 1520. The vacuum head base is also a tubular structure which has a significantly larger inside diameter than the outside diameter of the distal portion of functional block 1518, so as to form an annulus or annular space 1526 therebetween. Treatment tip 1522 extends annular space 1526.

A passageway 1528 runs the full length of functional block 1518 and forms a continuation of the flow path defined by tube 1509 when the tube is connected to the proximal end of functional block 1518.

An abrasive member 1530 is formed at the distal end of functional block 1518 thereby closing off passageway 1528 at the distal end of functional block 1518. The abrasive member is formed by fusing abrasive particles to the end of the functional block 1518, or could alternatively be made as an abrasive disk and fitted within an open end of the functional block to seal the end or mounted to a closed end of functional block 1518. Although the abrasive member shown is substantially planar, it may alternatively be rounded, flared, concave, convex or elongated, for example. The abrasive particles are of a size ranging from about 50 grit to 300 grit, typically about 100 grit to 120 grit and are typically carborundum (aluminum oxide) or sodium bicarbonate, or the like. The coarser particles (at the lower ends of the grit ranges) may be provided on a functional block for use in initial treatments, while finer particles (at the higher ends of the grit ranges) may be employed for subsequent treatments.

Alternatively, the abrasive member may be formed by knurling, machining, laser treatment or otherwise mechanically or chemically treating a closed end of the functional block to form the abrasive end. One or more openings 1532 are provided through the wall of the distal tubular structure of functional block 1518 to establish one or more flow pathways between passageway 1528 and annulus 1526. Treatment tip 1522 extends beyond the extremity of functional block 1518 such that abrasive member 1530 is positioned internally of assembled hand piece 1505, and surrounded by annulus 1526.

An opening or port 1534 is provided in the vacuum head base 1520 for connection of a vacuum source, for example, by connecting vacuum port 1534 to the vacuum source via a vacuum line. When vacuum is applied through opening 1534, opening 1524 is sealed off, for example, by placing it up against skin tissue, a closed loop vacuum flow path is established between the vacuum source and connecting line, vacuum opening 1534, annulus 1526, one or more openings 1532, passage way 1528, and tube 1509. This flow path is shown in FIG. 15 as a dotted line 1560.

Figure 16:
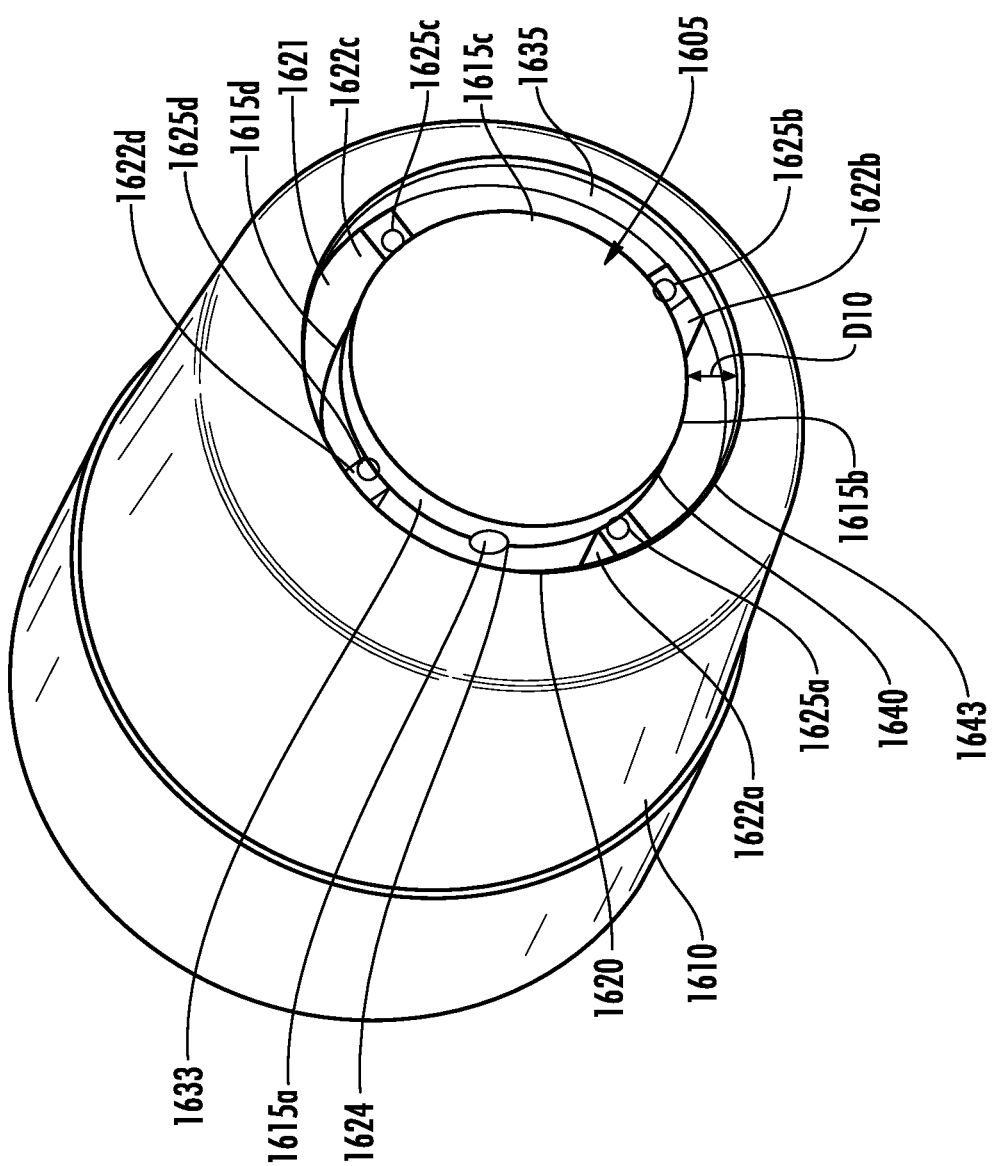
FIG. 16 shows a front view of an embodiment of a tip holder and abrasive tip.

FIG. 16 shows an example of an abrasive tip 1605 placed within a tip holder 1610. The tip holder may include one or more radiation sources such as radiation sources 1625a, 1625b, 1625c, and 1625d. Fluid flows out of one or more fluid openings such as fluid openings 1615a, 1615b, 1615c, and 1615d to treat the skin. An annular opening 1620 surrounds the abrasive tip and fluid openings. The annular opening is connected to an annular passageway 1621. Support ribs, such as 1622a, 1622b, 1622c, and 1622d help to support tube 1623 in the annular passageway.

As shown in the example in FIG. 16, a fluid opening includes an outer edge 1624 at a first position which is outside an edge or periphery 1640 of the abrasive surface. The fluid input opening (i.e., annular opening) includes an edge or outer edge 1643 at a second position, outside a periphery of the abrasive surface and is a greater distance away from the abrasive surface than the second position.

Figure 18:
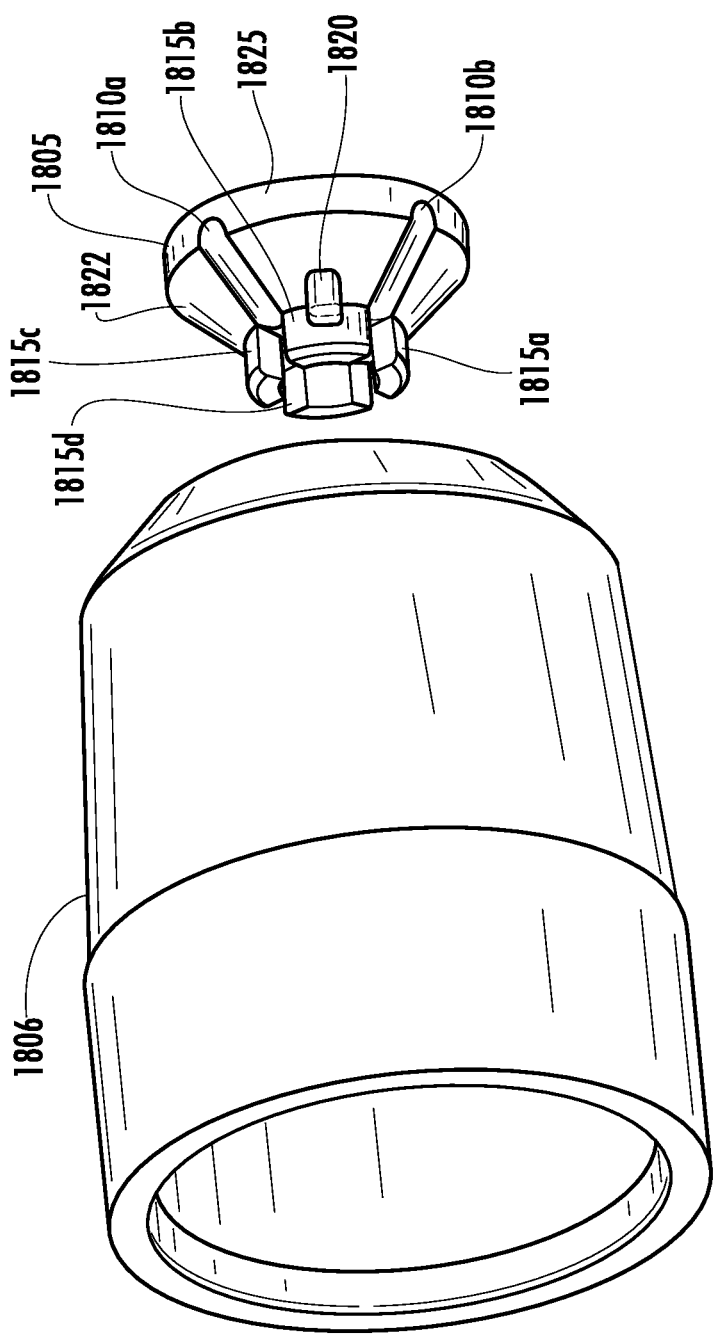
FIG. 18 shows a back view of an embodiment of the tip.

In a specific implementation, the abrasive tip includes an abrasive surface 1630, a side surface 1633, and a back side 1804 (see FIG. 18). An edge 1640 at the perimeter of the abrasive surface and an edge 1643 of the tip holder form the annular opening. That is, edge 1640 defines an inner edge and edge 1643 defines an outer edge. The annular opening is the region between the inner and outer edges. In an embodiment, the inner and outer edges are concentric circles. That is, edge 1640 (i.e., inner edge) is the inner circle and edge 1643 (i.e., outer edge) is the outer circle.

Side surface 1633 and an inner surface 1635 of the tip holder form the annular passageway. Fluids and abraded tissues are vacuumed or suctioned back into the wand or hand piece through the annular passageway. That is, a negative or low pressure region relative to ambient pressure is created in the annular passageway.

In a specific embodiment, the annular opening is on the same plane as the abrasive surface. However, in other embodiments, the annular opening is below or above the plane of the abrasive surface For example, the annular opening may range from about 0.5 millimeters to about 5 millimeters above or below the plane of the abrasive surface.

The annular opening includes a surface area A10 Surface area A10 is generally calculated by noting that a distance D10 is between edge 1640 of the abrasive tip and edge 1643 of the tip holder. That is, D10 indicates a width of the annular opening. In a specific embodiment where the abrasive surface and tip holder have circular cross sections, surface area A10 can be calculated using the equation below:

$$A10 = \pi \left[ \frac{\text{Diameter of abrading surface} + (2 * D10)}{2} \right]^2 - \pi \left[ \frac{\text{Diameter of abrading surface}}{2} \right]^2 \quad (1)$$

For example, in a specific embodiment, the diameter of the abrasive surface is about 9 millimeters and distance D10 is about 1.5 millimeters. Inserting these values in to equation (1) results in a value of about 49 square millimeters for surface area A10. In this specific embodiment, surface area A10 is less than the surface area of the abrasive surface which is about 64 square millimeters. Surface area A10 is about 23 percent less than the surface area of the abrasive surface, but may range from about 15 percent to about 30 percent less.

However, in other embodiments, surface area A10 of the annular opening is greater than the surface area of the abrasive surface. For example, in a specific embodiment, the diameter of the abrasive surface is about 6 millimeters and distance D10 is about 1.5 millimeters. Inserting these values into equation (1) results in a value of about 36 square millimeters for surface area A10. In this specific embodiment, surface area A10 is greater than the surface area of the abrasive surface which is about 28 square millimeters. Surface area A10 is about 28 percent greater than the surface area of the abrasive surface, but may range from about 15 percent to about 40 percent greater.

Generally, a larger surface area A10 of the annular opening or a larger distance D10 is desirable. This will help prevent potential blockage or other similar problems. That is, a larger surface area A10 or distance D10 allows fluid and other debris such as abraded skin particles to pass through without becoming wedged in the annular opening.

As discussed, in a specific embodiment, distance D10 is about 1.5 millimeters. But distance D10 may range from about 0.5 millimeters to about 10 millimeters. This includes, for example, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, or more than 10 millimeters, and less than 0.5 millimeters.

Distance D10 varies depending on the specific design or application. For example, in some cases a patient may have very dry and flaky skin. A microdermabrasion treatment for this particular patient may result in large pieces of skin being removed. Thus, a microdermabrasion wand with a large annular opening (e.g., large distance D10) will help to prevent the annular opening from becoming clogged with the large pieces of skin. As another example, a different patient may have normal skin that does not include flaky areas. In this case, a microdermabrasion wand with a smaller annular opening (e.g., smaller distance D10) may be used.

The abrasive tip or abrasive surface of the abrasive tip is typically made of an impermeable material that does not permit fluid (e.g., gas, air, and liquids) to flow or pass through. That is, the material is generally not a sponge or pad. In other words, in a specific embodiment, fluid from a fluid opening is placed on the abrasive surface without passing through the abrasive surface.

The abrasive tip is typically solid and may be made of, for example, plastics such as nylons, thermoplastics, polyethylene, polycarbonate, acrylonitrile butadiene styrene (ABS), metals such as stainless steel, aluminum, titanium, or brass.

Because the abrasive tip is typically designed so that fluid flows around it or through channels within it, there is less of a chance that the fluid flow will be restricted as compared to other materials such as sponges, pads or other membranes. In these other materials, fluid flows through small pores in the material and these small pores are more likely to become clogged.

The abrasive surface is generally formed by fusing (e.g., gluing and imbedding) abrasive particles to the surface. Examples of abrasive particles include diamond, silicone carbide, magnesium oxide, aluminum oxide, and the like, or combinations of these. The abrasive surface may also be formed by applying an adhesive-backed paper substrate to the surface, knurling, machining, laser treatment or otherwise mechanically or chemically treating the surface. The abrasive surface may also include an abrasive open screen with bonded abrasive particles.

Some embodiments of the abrasive tip include porous materials. For example, in a specific embodiment of the abrasive tip, the abrasive tip includes an abrasive mesh or web.

The side surface is at an angle to the abrasive surface. In a specific embodiment, the side surface is at a 90-degree angle (i.e., perpendicular) to the abrasive surface. One or more fluid openings (1615a-d) are at least partially formed on the side surface. There can be any number of fluid openings. For example, there may be one fluid opening, two fluid openings, or three or more fluid openings such as four fluid openings as shown in the example of FIG. 16. In a specific embodiment, these fluid openings are evenly distributed around the abrasive tip. For example, an angle between the fluid openings is given by 360 degrees divided by the total number of fluid openings (e.g., two fluid openings, the angle is 180 degrees, three fluid openings, the angle is 60 degrees, four fluid openings, the angle is 90 degrees; and for five fluid openings, the angle is 72 degrees).

Since the side surface is at an angle to the abrasive surface, these fluid openings may also be at an angle relative to the abrasive surface. For example, the fluid openings may be perpendicular to the abrasive surface as shown in the example in FIG. 16. In other words, a line passing through the perimeter of a fluid opening intersects a plane on which the abrasive surface lies.

One benefit of this orientation of the fluid openings to the abrasive surface is that there is less of a chance that the fluid openings will become blocked by the tissue surface. The fluids exit from the fluid openings, into the annular passageway, and out the annular opening. The fluids are free to flow directly to the skin without having to first flow through any sponge, pad, or other membrane or porous material. For example, during use, the abrasive surface contacts the skin surface. At this point, the skin surface and abrasive surface all lie on the same plane. The fluid openings, however, are at an angle to that plane and are thus unlikely to become blocked by the skin surface. The fluid then flows back into the annular opening and into the annular passageway.

As another feature, fluid deposited on the abrasive surface from a single fluid opening is capable of being drawn into the annular opening from one, two, three or more than three directions. Two or more directions may be opposite to each other, transverse to each other, or both. For example, as the user runs the abrasive tip over the patient's skin, fluid exits from the fluid openings such as fluid opening 1615a. The suction in the annular opening and the movement of the tip across the skin surface allows the fluid or a portion of the fluid to flow across or spread out over the abrasive surface and treat the target skin. The fluid can then be drawn into the annular opening. In some cases, the fluid exiting fluid opening 1615a will travel the furthest distance across the tip (e.g., diameter of a circular tip and diagonal of a square or rectangular tip) before being drawn into the annular opening. In other cases, the fluid exiting fluid opening 1615a will travel a shorter distance across the tip (e.g., cord of a circular tip and side of a square or rectangular tip).

Furthermore, this orientation allows the fluid flow to operate independently of the force that the user applies to the hand piece. For example, if the user applies a large amount of force to the hand piece to produce a large amount of abrasion, the fluid openings will not become blocked or constricted and fluid will continue to freely flow and treat the skin. For example, the fluid openings will not become smaller or compressed since the fluid openings are formed from rigid materials (e.g., plastic).

Although FIG. 16 shows the annular opening, passageway and tube having circular shapes, other embodiments have different shapes or combinations of different shapes. Some examples of other shapes include squares, rectangles, ovals, and triangles.

Figure 17:
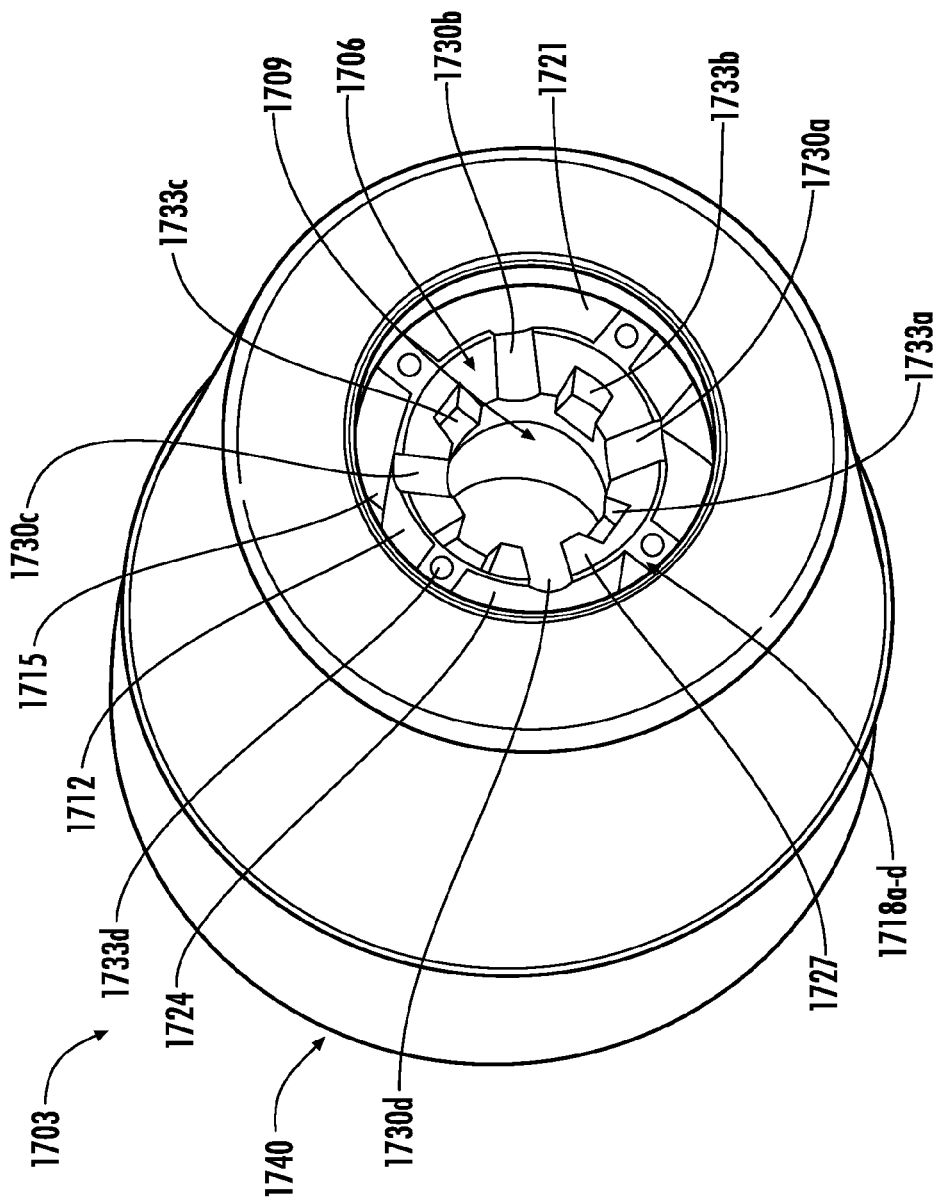
FIG. 17 shows a front view of an embodiment of the tip holder.

FIG. 17 shows a front view of a specific implementation of a tip holder 1703 that includes a recess 1706 at a distal end 1709 of a tube 1712. The abrasive tip fits into the recess. The tube is surrounded by an annular space or passageway 1715. The annular passageway may be interrupted by one or more support ribs 1718a-d which span from an inner surface 1721 of the tip holder to an outer surface 1724 of the tube.

The recess includes a surface 1727 which in turn includes features that help position the abrasive tip and direct fluid flow around the abrasive tip. Typically, the abrasive tip is positioned such that it is centered on the tube. For example, a longitudinal axis passing through the center of the tube will also pass through a center of the abrasive tip. However, in other embodiments, the abrasive tip is offset from the tube.

The features that help position the abrasive tip and direct fluid flow around the tip include one or more channels such as channels 1730a, 1730b, 1730c, and 1730d. These features also include one or more notches such as notches 1733a, 1733b, 1733c, and 1733d.

There may be any number of channels (e.g., no channels, one, two, three, four, five, or more than five channels). In an embodiment, the channels are evenly distributed about a lumen 1736 of the tube. For example, an angle between the channels is given by 360 degrees divided by the total number of channels openings (e.g., two channels, the angle is 180 degrees, three channels, the angle is 60 degrees, four channels, the angle is 90 degrees; and for five channels, the angle is 72 degrees).

The channels in the recess align with channels in the abrasive tip to form the fluid openings. The notches in the recess help to position the abrasive tip so that the fluid openings can be formed. That is, the notches mate with keys on the abrasive tip.

In an embodiment, the surface of the recess is at an oblique angle relative to the outer surface of the tube. Typically, that angle is an acute angle. This allows fluid to flow through the lumen of the tube and out the distal end where the fluid is divided via the channels and directed along the channels and to a periphery of the abrasive tip. The fluid is then vacuumed or suctioned into the annular passageway.

The tube is positioned within the annular passageway. In a specific embodiment, the tube and annular passageway are positioned to form concentric circles. That is, the tube and annular passageway share a common center axis and the annular passageway encircles the abrasive surface. For example, a lateral cross section through the tip holder shows an inner circle (i.e., tube) and an outer circle (i.e., annular passageway) having a diameter that is greater than the diameter of the inner circle (i.e., tube). The inner and outer circles are concentric. A fluid flow is through the tube, through the fluid openings, into the annular passageway, out the annular opening, and then back into the annular opening and annular passageway. In other words, fluids pass out of and back into the same opening, i.e., the annular opening.

In this specific embodiment, the pressure in the lumen of the tube is greater than the pressure in the annular passageway. That is, the annular passageway includes a region of pressure which at least partially surrounds the tube. The region of pressure is less than the pressure in the lumen of the tube. This pressure differential at least partially contributes to the fluid flow through the lumen of the tube, out the distal end of the tube, and then back into the hand piece through the annular passageway.

In another embodiment, the fluid flow is reversed. That is, fluid flows through and out the annular passageway and then flows into the lumen of the tube.

In a specific embodiment, the fluid in the lumen is a liquid rather than a gas. That is, the fluid is incompressible. However, in other embodiments, the fluid includes gases as well.

The tip holder may be designed so that the abrasive tip can rest or sit on the tip holder. Specifically, the abrasive tip may rest or sit on the recess of the tip holder rather than being placed between the tip holder and some other member of the microdermabrasion hand piece. This makes the abrasive tip easy to replace since it allows the user to remove the abrasive tip and insert a new abrasive tip without having to also remove the tip holder. However, in other implementations, as shown, for example, in FIG. 19, the abrasive tip is placed between the tip holder and another member of the microdermabrasion hand piece.

It should be appreciated that any arrangement or number of support ribs (including no support ribs) is possible so long as fluids are able to pass through the vacuum created in the annular passageway.

Consequently, a flange, or a portion of a flange may be used between the inner surface of the tip holder and the outer surface of the tube, either with or without support ribs. For example, where a flange completely encircles the tube, the flange may contain one or more openings which allow fluids to pass from the front of the tip holder to the back of the tip holder.

The tip holder may be formed using any number of manufacturing techniques. Some examples include machining, casting, molding, injection molding, etching, or combinations of these.

In a specific embodiment, the outer width (e.g., outer diameter) of the tip holder tapers or decreases from a proximal end 1740 of the tip holder to the distal end of the tube. This may also result in a tapering or decrease of the cross-sectional area of the annular passageway from proximal end 1740 to the distal end of the tube. However, in other embodiments the cross-sectional area of the annular passageway remains constant regardless of whether the outer diameter of the tip holder tapers. For example, the walls of the tip holder may have a thickness that varies. The walls of the tip holder may be thicker at the proximal end of the tip holder than at the distal end of the tube. Thus, a cross-sectional area taken at a point between the proximal and distal ends may be the same as a cross-sectional area taken at a different point between the proximal and distal ends.

FIG. 18 shows a view of the back side of a specific implementation of an abrasive tip 1805 that fits into a tip holder 1806. In this implementation, the abrasive tip 1805 includes channels 1810a, 1810b, 1810c, and 1810d. Channels 1810c and 1810d are not shown due to the perspective view of the drawing. Abrasive tip 1805 also includes collars 1815a, 1815b, 1815c, and 1815d and a key 1820.

In a specific implementation, the channels 1810a, 1810b, 1810c, and 1810d are equally spaced around the perimeter of the abrasive tip. For example, in an implementation where the abrasive tip has a circular cross section and four channels, the channels may be located at 0, 90, 180, 270, and 360 degrees. In other implementations, the abrasive tip may include less than four channels, such as no channels, one channel, two channels, or three channels. In another implementation, there may be more than four channels, including, for example, five, six, seven, eight, or more than eight channels.

The channels are recessed into a conical surface 1822 on the back side of the tip. An angle between the conical surface and the abrasive surface is typically less than 90 degrees. For example, the angle may range from about 20 degrees to about 80 degrees. This includes less than 20 degrees, 30, 40, 45, 50, 60, 70, or more than 80 degrees. The conical surface starts at the cylindrical surface of the collars and spreads out towards the front of the tip. The channels extend outwardly through the collars towards the front of the tip. In a specific implementation, the channels terminate on a side surface 1825 of the tip. In another implementation, the channels may continue through to the front of the tip.

Channels 1810a, 1810b, 1810c, and 1810d in the abrasive tip align with channels 1730a, 1730b, 1730c, and 1730d in the tip holder as shown in FIG. 17. When these channels are aligned they form the openings 1615a, 1615b, 1615c, and 1615d as shown in FIG. 16 that fluid flows out of. For example, with reference to FIGS. 16, 17, and 18, channel 1810a in the abrasive tip aligns with channel 1730a in the tip holder to form opening 1615a. Channel 1810b in the abrasive tip aligns with channel 1730b in the tip holder to form opening 1615b. Channel 1810c in the abrasive tip aligns with channel 1730c in the tip holder to form opening 1615c. Channel 1810d in the abrasive tip aligns with channel 1730d in the tip holder to form opening 1615d.

FIG. 18 shows U-shaped or semi-circular shaped channels which, when aligned, form circular shaped openings. However, this is not always the case. In other implementations, the openings formed may have the shape of a polygon such as a rectangle or square, or the shape may be elliptical or oval. Furthermore, there may be a combination of differently shaped openings which are formed using differently shaped channels.

In a specific implementation, the openings allow fluid to flow out around the perimeter of the abrasive tip as opposed to the front surface of the abrasive tip. This prevents the tissue that is being treated from occluding the openings.

However, in other implementations, there may be openings on the surface of the abrasive tip itself. For example, there may be an opening for fluid located in the center of the abrasive tip. Additionally, there may also be a combination of openings at different locations. For example, there may be openings located at or near the perimeter of the abrasive tip and an opening or openings on the surface of the abrasive tip.

In a specific implementation, the openings all have the same cross-sectional areas. The total cross-sectional area of the openings is less than the surface area of the abrasive surface. For example, the total cross-sectional area of the opening may be about 20 to about 60 percent less than the surface area of the abrasive surface.

Each cross-sectional area of an opening may range, for example, from about 0.05 square millimeters to about 20 square millimeters. For example, the cross-sectional areas may be 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.5, 4, 4.5, 5, 10, 15, or 19.9 square millimeters. Depending on the application, the cross-sectional area may be less than 0.05 square millimeters, or greater than 20 square millimeters. In other implementations, the cross-sectional areas of the openings will be different. For example, one opening may have a cross-sectional area of 0.03 square millimeters, while another opening may have a cross-sectional area of 0.05 square millimeters.

In yet another implementation, the cross-sectional area of a particular opening may vary from one end of the opening to the opposite end. This allows, for example, varying the flow rate and velocity of fluid exiting from the openings.

In a specific implementation, key 1820 in the abrasive tip fits into any of notches 1733a, 1733b, 1733c, and 1733d in the tip holder as shown in FIG. 17. Thus, this specific implementation provides for four different positions for the abrasive tip to be positioned in tip holder.

There may be any number of keys. For example, there may be no keys, one, two, three, four, five, or more than five keys. In a specific implementation, the number of keys on the abrasive tip is the same as the number of notches on the tip holder. In another implementation, the number is different. For example, there may be fewer keys on the abrasive tip than notches on the tip holder.

In a specific implementation, the sizes of the keys and notches are the same. In another implementation, the sizes are different. In yet another implementation, the notches are on the abrasive tip while the keys are on the tip holder, or there may be a combination arrangement. That is, an implementation includes a combination of keys and notches on both the abrasive tip and tip holder.

The key or keys ensure that channels 1730a, 1730b, 1730c, and 1730d in the tip holder (see FIG. 17) and channels 1810a, 1810b, 1810c, and 1810d in the abrasive tip are properly aligned to form openings 1615a, 1615b, 1615c, and 1615d (see FIG. 16) through which fluid flows out.

In a specific implementation, the keys are used to specifically misalign certain channels in the tip holder and abrasive tip in order to not form an opening for fluid to exit. Thus, the amount of fluid exiting may be adjusted by misaligning the channels in the abrasive tip with the channels in the tip holder.

In a specific implementation where there is a particular direction of travel for the abrasive tip, the keys may also be used to ensure that the abrasive tip is properly positioned along the particular direction of travel. For example, the abrasive tip may include two regions having different grits such as coarse and fine grits. A microdermabrasion treatment may include treatment with the coarse grit followed by the fine grit. Thus, the user will run the hand piece over the patient's tissue so that the tissue is first treated by the coarse grit region of the abrasive tip.

Collars 1815a, 1815b, 1815c, and 1815d slide into the tip holder. Collars 1815a, 1815b, 1815c, and 1815d are positioned between channels 1810a, 1810b, 1810c, and 1810d in the abrasive tip. This allows fluid to flow out of the openings formed by aligning the channels in the abrasive tip with the channels in the tip holder. The collars protrude from the back side of the tip.

The number of collars may vary. Typically, the number of collars will be dependent on the number of channels. For example, if there are four channels, then there will be four collars. However, this is not always the case. In other implementations, the number of collars will be different from the number of channels. There may be more channels than collars, or there may be fewer channels than collars.

Figure 19:
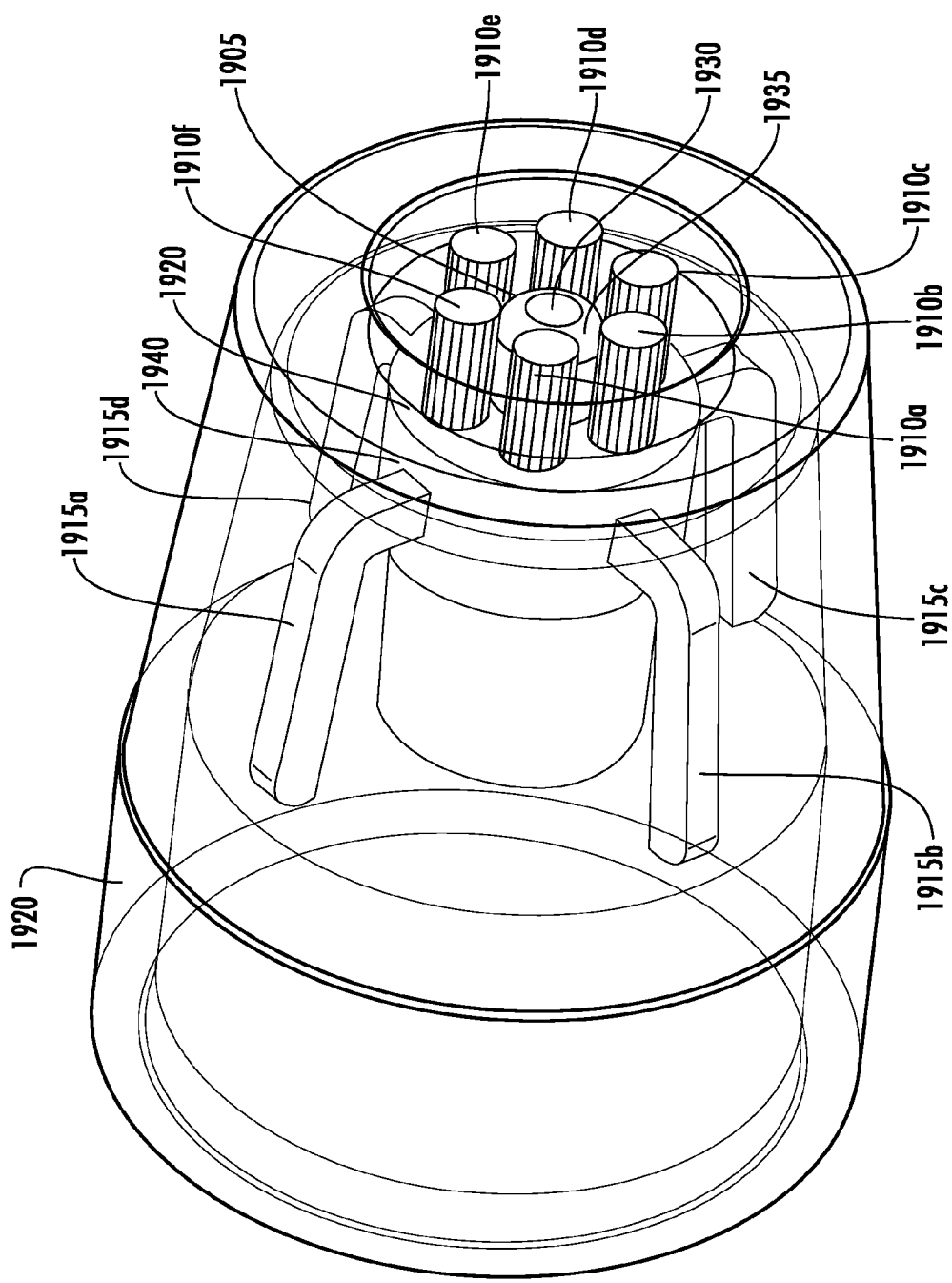
FIG. 19 shows an embodiment of a bristled tip.

FIG. 19 shows an example of a specific implementation of a bristled tip 1905. In a specific implementation, bristled tip 1905 includes six groups of bristles (1910a, 1910b, 1910c, 1910d, 1910e, 1910f), four support ribs or prongs (1915a, 1915b, 1915c, 1915d) which are offset from a face 1920 of the bristled tip, and an opening 1930 which is at the end of a nipple 1935.

In one embodiment, one or more bristles is connected to a radiation source. For example, the bristle may be coupled to an LED. The bristle may act as a waveguide for directing radiation from the radiation source and into the tissue. Thus, in a specific implementation, the bristle is made of optical fiber.

In yet another embodiment, one or more bristles are translucent so that the bristles do not block any light that may be transmitted from the radiation sources into the patient's tissue. Thus, in specific embodiments, light is transmitted through an area of tissue that is being abraded.

Although FIG. 19 shows six groups of bristles, the number of groups of bristles varies. For example, other implementations include one, two, three, four, five, or more than six groups of bristles.

Nipple 1935 extends some distance away from face 1920 of the bristled tip. The opening may extend from about 30 percent to about 75 percent the length of the bristles, including, for example, less than 30 percent, 50 percent, or more than 75 percent the length of the bristles.

In an implementation, fluid flows through the nipple and out the opening. The nipple places opening 1930 closer to the skin and helps to ensure that the fluid contacts the skin before being pulled back into tip holder 1920.

Support ribs or prongs 1915a, 1915b, 1915c, and 1915d may be offset from face 1920 of the bristled tip and attached at any point along the length of the bristled tip. In a specific implementation, the distance for the offset is the same for all support ribs 1915a, 1915b, 1915c, and 1915d. In other implementations, the support ribs are offset at different distances. For example, support rib 1915a may be offset from face 1920 by 0.5 millimeters, while support ribs 1915a, 1915b, and 1915c may be offset from face 1920 by 1 millimeter.

Offsetting the support ribs allows, for example, an uninterrupted annular space 1940 to be created near the front of the tip holder 1920. This allows fluids to more easily pass back into tip holder 1920 without being blocked by any structures. However, other implementations may have the support ribs or prongs flush with face 1920.

The support ribs or prongs extend outwardly and then turn to splay longitudinally down the length of the bristled tip.

Although FIG. 19 shows four prongs, the number of prongs may vary. For example, other implementations include one, two, three, five, six, seven, or more than eight prongs.

It should be appreciated that there may be many different combinations of bristled tips that include, for example, different numbers of bristle groups, support ribs and fluid openings, different attachment positions for support ribs, or different positions for fluid openings. For example, in a specific implementation, the bristled tip includes three support ribs flush with face 1920 and six groups of bristles. In another configuration, the support ribs are not be equally spaced from each other. For example, instead of being spaced at 0 degrees and 180 degrees, the support ribs are spaced at 0 degrees and 92 degrees. Furthermore, a first support rib is attached flush with the face of the bristled tip while a second support rib is offset 0.5 millimeters, for example, from the face of the bristled tip.

Figure 20:
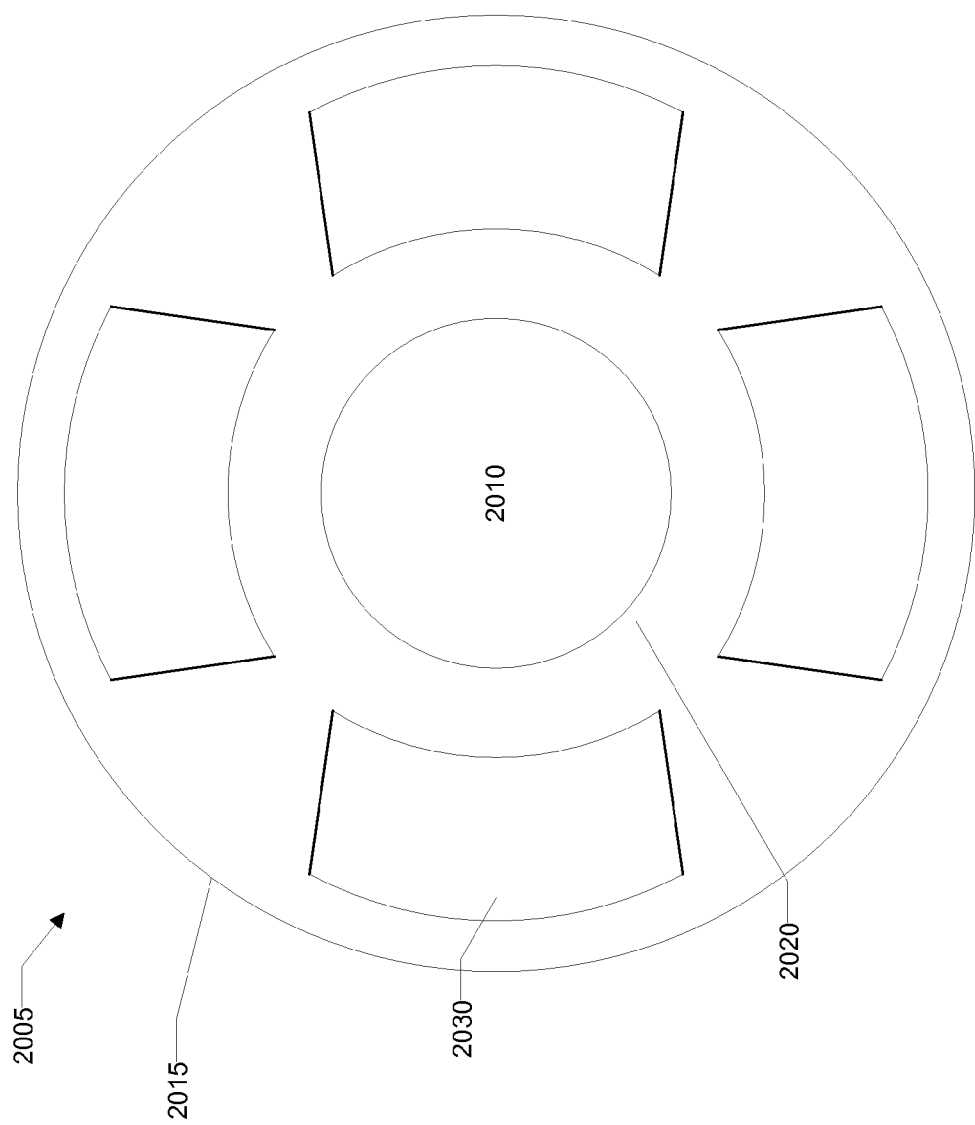
FIG. 20 shows a front view of an embodiment of a hand piece with arc-shaped vacuum openings.

FIG. 20 shows a partial front view of another embodiment of a hand piece 2005 including a tip 2010 and a tip holder 2015. One or more fluid openings 2020 are positioned outside a periphery 2025 of the abrasive tip. The fluid openings output fluid. One or more vacuum openings 2030 are also positioned outside the periphery of the abrasive tip and are positioned at a further distance away from the abrasive tip than the fluid output openings.

As shown, the vacuum openings are at least partially around the abrasive tip. The vacuum openings may be connected to one or more vacuum lines. Although FIG. 20 shows the vacuum openings as having arc shapes, other embodiments may include differently shaped vacuum openings such as square, rectangular, circular, oval, or triangular openings.

In other embodiments, the fluid flow is reversed. That is instead of fluid opening 2020 outputting fluid and vacuum opening 2030 inputting fluid, fluid opening 2020 accepts fluid input and vacuum opening 2030 outputs fluid.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A microdermabrasion system upgrade kit comprising:
a container, comprising a plurality of couplers, wherein a first and second coupler have a first end with the same coupler diameter, and a second end of the first coupler has a different diameter than a second end of the second coupler;
a console comprising a power socket that is capable of outputting power, a first switch, coupled to a supply line providing power,
a second switch, coupled between the supply line and the power socket, and
a second switch control circuit, coupled to the supply line and the second switch,
wherein the second switch control controls the second switch such that in a first mode, the second switch passes power from the supply line to the power socket, and in a second mode, the second switch disconnects power from the supply line to the power socket, and
while in the second mode, the second switch control circuit is supplied with power passing through the first switch; and
a microdermabrasion hand piece, coupled to the console, comprising:
a replaceable abrasive tip having a surface bonded with abrasive particles to form an abrasive surface;
at least one fluid output opening having an outer edge at a first position outside a periphery of the abrasive surface; and
at least one fluid input opening having an outer edge at a second position outside a periphery of the abrasive surface, wherein the second position is a greater distance away from the abrasive surface than the first position.

2. The kit of claim 1 wherein the fluid input opening couples to a first passageway, the fluid output opening couples to a second passageway, and the first passageway has a greater diameter than the second passageway.

3. The kit of claim 1 wherein the fluid input opening couples to a first tubular passageway, the fluid output opening couples to a second tubular passageway, and the first and second tubular passageways share a common center axis.

4. The kit of claim 1 wherein the fluid input opening couples to a first tubular passageway, the fluid output opening couples to a second tubular passageway, and the second passageway is within the first passageway.

5. The kit of claim 1 wherein fluid deposited on the abrasive tip from the one fluid output opening is capable of being drawn into the one fluid input opening from at least two different directions, opposite of one another.

6. The kit of claim 1 wherein fluid deposited on the abrasive tip from the one fluid output opening is capable of being drawn into the one fluid input opening from at least two different directions, transverse to one another.

7. The kit of claim 1 wherein fluid deposited on the abrasive tip from the one fluid output opening is drawn into the one fluid input opening without passing through a porous material.

8. The kit of claim 1 wherein fluid from the one fluid output opening is placed on the abrasive surface without passing through the abrasive surface.

9. The kit of claim 1 wherein the one fluid input opening encircles the abrasive surface.

10. The kit of claim 1 comprising:
a second fluid input opening having an outer edge at a third position outside a periphery of the abrasive surface, wherein the third position is a greater distance away from the abrasive surface than the first position, and the third position is on an opposite side of the abrasive surface from the second position.

11. The microdermabrasion system upgrade kit of claim 1 wherein the microdermabrasion system upgrade kit does not comprise a vacuum pump.

12. The microdermabrasion system upgrade kit of claim 1 wherein when the first coupler is removed from the container and coupled in series with a vacuum line coupled to the microdermabrasion hand piece, the second coupler is not coupled to the vacuum line in series or in parallel.

13. The microdermabrasion system upgrade kit of claim 1 wherein the first and second ends of the first and second couplers comprise male fittings that can be inserted into vacuum tubing.

14. The microdermabrasion system upgrade kit of claim 1 wherein the replaceable abrasive tip is a first replaceable abrasive tip and can be removed from the microdermabrasion hand piece and replaced with a second replaceable abrasive tip comprising abrasive bristles.

15. The microdermabrasion system upgrade kit of claim 1 wherein the abrasive surface of the replaceable abrasive tip is relatively planar.

16. A microdermabrasion system upgrade kit comprising:
a container, comprising a plurality of couplers, wherein a first and second coupler have a first end with the same coupler diameter, and a second end of the first coupler has a different diameter than a second end of the second coupler;
a console comprising a power socket that is capable of outputting power; a first switch, coupled to a supply line supplying power; a second switch, coupled between the supply line and the power socket; a security circuit, coupled to the supply line and the second switch, and a vacuum tube input line having a diameter to fit the first ends of the first and second couplers,
wherein the security circuit controls an operation of the second switch, and in a first mode, the second switch couples power from the supply line to the power socket, and in a second mode, the second switch disconnects power from the supply line to the power socket, and
while in the second mode, the security circuit is supplied with power passing through the first switch; and a microdermabrasion hand piece, coupled to the console and the vacuum tube input line.

17. The kit of claim 16 wherein the container comprises a base member, a reclosable lid, and a tray that fits in the base member, the tray having a first cavity to hold the first coupler and a second cavity to hold the second coupler.

18. The kit of claim 17 wherein in the tray, adjacent to the first cavity is first label and adjacent to the second cavity is a second label, different from the first label.

19. The kit of claim 16 comprising an instruction manual and video disc, wherein the video disc has a video presentation showing how to connect the console to a vacuum pump external to the console.

20. The microdermabrasion system upgrade kit of claim 16 wherein the microdermabrasion system upgrade kit does not comprise a vacuum pump.

21. A microdermabrasion system upgrade kit comprising:
a container, comprising a plurality of couplers, wherein a first and second coupler have a first end with the same coupler diameter, and a second end of the first coupler has a different diameter than a second end of the second coupler;
a console housing comprising a power socket that is capable of outputting power, a first switch, coupled to a supply line supplying power, a second switch, coupled between the supply line and the power socket, and a second switch control circuit, coupled to the supply line and the second switch, wherein the second switch control circuit controls the second switch such that in a first mode, the second switch passes power from the supply line to the power socket, and in a second mode, the second switch disconnects power from the supply line to the power socket, and while in the second mode, the second switch control circuit is supplied with power passing through the first switch, wherein the console housing does not include a vacuum pump; and a microdermabrasion hand piece, coupled to the console housing.

22. The kit of claim 21 wherein turning on the first switch turns on a vacuum pump pressure display of the console and the power socket.

23. The kit of claim 21 wherein an enclosure of the console has dimensions which are insufficient for housing a vacuum pump.

24. The kit of claim 21 wherein an enclosure of the console does not have a forced air output vent that is coupled to the hand piece.

25. The kit of claim 21 comprising an instruction manual and video disc, wherein the video disc has a video presentation showing how to connect the console to a vacuum pump external to the console.

26. A microdermabrasion system upgrade kit comprising:
a container, comprising a plurality of couplers, wherein a first and second coupler have a first end with the same coupler diameter, and a second end of the first coupler has a different diameter than a second end of the second coupler;
a console comprising a power socket that is capable of outputting power, and a first switch, coupled to a supply line supplying power, wherein the microdermabrasion system upgrade kit does not include a vacuum pump;
a microdermabrasion hand piece, coupled to the console, wherein turning on the first switch turns on a vacuum pump pressure display of the console and the power socket,
wherein the console comprises:
a second switch, coupled between the supply line and the power socket, and
a second switch control circuit, coupled to the supply line and the second switch,
wherein the second switch control circuit controls the second switch such that in a first mode, the second switch passes power from the supply line to the power socket, and in a second mode, the second switch disconnects power from the supply line to the power socket, and
while in the second mode, the second switch control circuit is supplied with power passing through the first switch.

27. A microdermabrasion system upgrade kit comprising:
a container, comprising a plurality of couplers, wherein a first and second coupler have a first end with the same coupler diameter, and a second end of the first coupler has a different diameter than a second end of the second coupler;
a console comprising a power socket that is capable of outputting power, a first switch, coupled to a supply line supplying power, a second switch, coupled between the supply line and the power socket, and a second switch control circuit, coupled to the supply line and the second switch,
wherein the second switch control circuit controls the second switch such that in a first mode, the second switch passes power from the supply line to the power socket, and in a second mode, the second switch disconnects power from the supply line to the power socket,
while in the second mode, the second switch control circuit is supplied with power passing through the first switch, and
the microdermabrasion system upgrade kit does not include a vacuum pump; and
a microdermabrasion hand piece, coupled to the console.

28. The microdermabrasion system upgrade kit of claim 27 wherein a housing of the console does not include the vacuum pump.

* * * * *